United States Patent
Iida et al.

(10) Patent No.: US 12,007,317 B2
(45) Date of Patent: Jun. 11, 2024

(54) MICROSCOPIC OBJECT COLLECTION SYSTEM AND MICROSCOPIC OBJECT COLLECTION METHOD

(71) Applicants: University Public Corporation Osaka, Osaka (JP); Murata Manufacturing Co., Ltd., Nagaokakyo (JP)

(72) Inventors: Takuya Iida, Sakai (JP); Shiho Tokonami, Sakai (JP); Hiroki Ishikawa, Nagaokakyo (JP); Tsutomu Yamasaki, Nagaokakyo (JP)

(73) Assignees: UNIVERSITY PUBLIC CORPORATION OSAKA, Osaka (JP); MURATA MANUFACTURING CO., LTD., Kyoto (JP)

( * ) Notice: Subject to any disclaimer, the term of this patent is extended or adjusted under 35 U.S.C. 154(b) by 429 days.

(21) Appl. No.: 17/606,183

(22) PCT Filed: Apr. 22, 2020

(86) PCT No.: PCT/JP2020/017348
§ 371 (c)(1),
(2) Date: Oct. 25, 2021

(87) PCT Pub. No.: WO2020/218346
PCT Pub. Date: Oct. 29, 2020

(65) Prior Publication Data
US 2022/0178798 A1    Jun. 9, 2022

(30) Foreign Application Priority Data

Apr. 25, 2019 (JP) .................................. 2019-084001

(51) Int. Cl.
*G01N 1/40* (2006.01)
*G01N 1/10* (2006.01)
(Continued)

(52) U.S. Cl.
CPC ............. *G01N 1/4022* (2013.01); *G01N 1/10* (2013.01); *H01S 5/022* (2013.01); *G01N 2001/1025* (2013.01); *G01N 2001/4027* (2013.01)

(58) Field of Classification Search
CPC ............ G01N 1/38; G01N 1/286; G01N 1/10; G01N 1/04; G01N 1/20; G01N 1/2035;
(Continued)

(56) References Cited

U.S. PATENT DOCUMENTS

| 2001/0030983 A1 | 10/2001 | Yuri et al. |
| 2003/0002783 A1 | 1/2003 | Neilson et al. |

(Continued)

FOREIGN PATENT DOCUMENTS

| CA | 2793840 A1 | 4/2014 |
| CN | 1393711 A | 1/2003 |

(Continued)

OTHER PUBLICATIONS

Official Communication issued in International Patent Application No. PCT/JP2020/017348, mailed on Jul. 21, 2020.
(Continued)

*Primary Examiner* — Andre J Allen
(74) *Attorney, Agent, or Firm* — Keating & Bennett, LLP

(57) ABSTRACT

A laser module includes a plurality of light emission regions and the plurality of light emission regions emit a plurality of laser beams. An optical waveguide and a lens condense the plurality of laser beams to an identical focal point. An adjustment mechanism is configured to adjust relative positional relation between the sample stage and a condenser lens (the optical waveguide and the lens). A controller is configured to switch between a single-point irradiation mode and a multi-point irradiation mode. The single-point irradiation mode refers to a mode in which the adjustment
(Continued)

mechanism is controlled such that the focal point of the plurality of laser beams falls on the thin film. The multi-point irradiation mode refers to a mode in which the adjustment mechanism is controlled such that the focal point does not fall on the thin film.

7 Claims, 30 Drawing Sheets

(51) Int. Cl.
    *G01N 1/44*     (2006.01)
    *H01S 5/022*     (2021.01)

(58) Field of Classification Search
CPC .. G01N 1/28; G01N 1/24; G01N 1/14; G01N 35/1097; G01N 1/00; G01N 1/2247; G01N 1/2252; G01N 35/1016; G01N 1/405; G01N 33/24; G01N 1/02; G01N 1/08; G01N 2001/028; G01N 2001/2264; G01N 1/18; G01N 1/22; G01N 1/36; G01N 2001/2223; G01N 1/2226; G01N 2001/1037; G01N 2035/00237; G01N 35/04; G01N 35/1011; G01N 1/2273; G01N 1/40; G01N 21/645; G01N 33/0011; G01N 2035/1025; G01N 35/026; G01N 2001/2866; G01N 2035/1032; G01N 35/00; G01N 35/08; G01N 35/1074; G01N 1/32; G01N 2001/021; G01N 2001/2873; G01N 27/44743; G01N 35/1002; G01N 1/2202; G01N 1/26; G01N 1/2813; G01N 15/1404; G01N 21/6428; G01N 21/85; G01N 27/44791; G01N 30/32; G01N 33/18; G01N 1/12; G01N 1/2205; G01N 1/4022; G01N 1/42; G01N 1/44; G01N 15/06; G01N 15/0618; G01N 2001/022; G01N 2001/205; G01N 2001/2071; G01N 2001/2229; G01N 2021/8592; G01N 2035/00277; G01N 21/3504; G01N 21/359; G01N 21/6452; G01N 2201/062; G01N 2203/0298; G01N 27/622; G01N 33/346; G01N 33/491; G01N 33/54373; G01N 35/00029; G01N 35/0099; G01N 35/10; G01N 35/1009; G01N 35/1095; G01N 1/2294; G01N 1/312; G01N 2001/225; G01N 2001/4088; G01N 2015/0038; G01N 2021/3545; G01N 2021/399; G01N 2035/00524; G01N 2035/102; G01N 21/0332; G01N 21/64; G01N 2201/1215; G01N 2291/02836; G01N 33/12; G01N 35/0092; G01N 35/025; G01N 35/1065; G01N 35/1079; G01N 1/2208; G01N 1/30; G01N 1/31; G01N 15/14; G01N 15/1429; G01N 15/1434; G01N 15/1456; G01N 2001/2057; G01N 2001/2285; G01N 2001/288; G01N 2001/383; G01N 2013/006; G01N 2015/1402; G01N 2015/1447; G01N 2015/1452; G01N 2030/326; G01N 2035/00673; G01N 2035/041; G01N 2035/103; G01N 21/07; G01N 21/3563; G01N 21/6458; G01N 2201/02; G01N 2201/06113; G01N 2201/0697; G01N 2203/027; G01N 2291/0256; G01N 2291/0426; G01N 29/022; G01N 3/02; G01N 30/24; G01N 33/0016; G01N 33/02; G01N 33/53; G01N 35/00732; G01N 35/1072; G01N 1/125; G01N 1/2214; G01N 1/2258; G01N 2001/1043; G01N 2001/1427; G01N 2035/00554; G01N 2035/1018; G01N 2203/0075; G01N 23/2204; G01N 30/02; G01N 33/20; G01N 33/241; G01N 33/2823; G01N 1/06; G01N 1/16; G01N 1/4044; G01N 1/4077; G01N 13/00; G01N 15/0255; G01N 15/05; G01N 15/065; G01N 15/10; G01N 2001/1012; G01N 2001/105; G01N 2001/1093; G01N 2001/1445; G01N 2001/2241; G01N 2001/2886; G01N 2001/4061; G01N 2015/1413; G01N 2030/025; G01N 2033/0077; G01N 2033/0091; G01N 2033/0093; G01N 2035/00326; G01N 2035/00495; G01N 2035/00534; G01N 2035/00752; G01N 2035/00782; G01N 2035/00891; G01N 2035/0465; G01N 2035/0481; G01N 2035/0484; G01N 2035/1037; G01N 2035/1053; G01N 2035/1076; G01N 2223/076; G01N 2291/0255; G01N 2291/0423; G01N 2291/0427; G01N 23/223; G01N 25/04; G01N 27/44704; G01N 27/44739; G01N 29/036; G01N 29/30; G01N 29/4436; G01N 3/22; G01N 3/56; G01N 33/0018; G01N 33/025; G01N 33/15; G01N 33/205; G01N 33/26; G01N 33/42; G01N 33/487; G01N 35/00663; G01N 35/00871; G01N 35/0098; G01N 7/14; G01N 1/34; G01N 11/16; G01N 15/02; G01N 15/0806; G01N 15/1409; G01N 15/1433; G01N 2001/1025; G01N 2001/1075; G01N 2001/1081; G01N 2001/1418; G01N 2001/2064; G01N 2001/2282; G01N 2001/244; G01N 2001/245; G01N 2015/1493; G01N 2021/0346; G01N 2030/009; G01N 2035/00039; G01N 2035/00148; G01N 2035/00316; G01N 2035/0405; G01N 2035/0406; G01N 2035/0425; G01N 2035/0429; G01N 2035/0493; G01N 21/01; G01N 21/05; G01N 23/207; G01N 27/447; G01N 29/222; G01N 30/20; G01N 31/12; G01N 31/22; G01N 33/0006; G01N 33/0026; G01N 33/0098; G01N 33/04; G01N 33/49; G01N 33/536; G01N 35/00693; G01N 35/021; G01N 35/085; G01N 1/2806; G01N 1/4055; G01N 11/04; G01N 11/10; G01N 15/0272; G01N 15/042; G01N 15/08; G01N 15/0826; G01N 15/0893; G01N 15/1484; G01N 15/149; G01N 17/00; G01N 2001/002; G01N 2001/005; G01N 2001/024; G01N 2001/1006; G01N 2001/1031; G01N 2001/1454; G01N 2001/2014; G01N 2001/2028; G01N 2001/2092; G01N 2001/2217; G01N 2001/2261; G01N 2001/2267; G01N 2001/2276; G01N 2001/2291; G01N 2001/242; G01N 2001/248; G01N 2001/282; G01N 2001/2826; G01N 2001/4016; G01N 2001/4066; G01N
2015/0019; G01N 2015/0049; G01N
2015/0057; G01N 2015/0096; G01N
2015/019; G01N 2015/025; G01N
2015/045; G01N 2015/0687; G01N
2015/084; G01N 2015/1006; G01N
2015/1411; G01N 2021/152; G01N
2021/5961; G01N 2021/6482; G01N
2021/6484; G01N 2021/845; G01N
2030/008; G01N 2030/162; G01N
2030/207; G01N 2030/285; G01N
2030/324; G01N 2030/383; G01N
2030/528; G01N 2030/565; G01N
2030/8854; G01N 2030/8881; G01N
2030/8886; G01N 2033/0095; G01N
2033/0096; G01N 2033/105; G01N
2033/245; G01N 2035/00049; G01N
2035/00188; G01N 2035/00306; G01N
2035/00356; G01N 2035/00455; G01N
2035/00772; G01N 2035/00801; G01N
2035/00851; G01N 2035/0091; G01N
2035/0408; G01N 2035/0415; G01N
2035/0434; G01N 2035/0449; G01N
2035/0458; G01N 2035/0462; G01N
2035/0467; G01N 2035/0491; G01N
2035/0496; G01N 2035/1034; G01N
2035/1041; G01N 2035/1058; G01N
2035/106; G01N 2035/1069; G01N
2035/1086; G01N 21/0303; G01N 21/15;
G01N 21/253; G01N 21/51; G01N 21/53;
G01N 21/59; G01N 21/6402; G01N
21/74; G01N 21/763; G01N 21/82; G01N
21/86; G01N 21/87; G01N 21/88; G01N
21/9508; G01N 2201/0846; G01N
2203/0007; G01N 2203/0044; G01N
2203/0048; G01N 2203/0055; G01N
2203/0064; G01N 2203/0073; G01N
2203/0085; G01N 2203/0242; G01N
2203/0244; G01N 2203/0252; G01N
2203/026; G01N 2203/0266; G01N
2203/0274; G01N 2203/0284; G01N
2291/015; G01N 2291/02475; G01N
2291/0422; G01N 2291/048; G01N
2291/103; G01N 2291/105; G01N 23/04;
G01N 23/16; G01N 23/2255; G01N
24/08; G01N 2500/00; G01N 2500/02;
G01N 27/023; G01N 27/12; G01N 27/38;
G01N 27/404; G01N 27/44721; G01N
2800/04; G01N 2800/30; G01N 29/048;
G01N 29/11; G01N 29/14; G01N 3/08;
G01N 3/12; G01N 3/28; G01N 3/307;
G01N 3/48; G01N 30/06; G01N 30/10;
G01N 30/12; G01N 30/16; G01N 30/30;
G01N 30/36; G01N 30/467; G01N 30/56;
G01N 30/6052; G01N 30/6082; G01N
30/6095; G01N 30/7266; G01N 30/80;
G01N 30/95; G01N 31/16; G01N
33/0001; G01N 33/0021; G01N 33/0027;
G01N 33/0031; G01N 33/10; G01N
33/1826; G01N 33/1893; G01N 33/2022;
G01N 33/28; G01N 33/2835; G01N
33/2888; G01N 33/343; G01N 33/365;
G01N 33/442; G01N 33/4833; G01N
33/48735; G01N 33/4875; G01N
33/4925; G01N 33/497; G01N 33/5302;
G01N 33/543; G01N 33/54366; G01N
33/60; G01N 33/6812; G01N 33/6848;
G01N 33/6893; G01N 33/6896; G01N
33/74; G01N 33/76; G01N 33/80; G01N
33/94; G01N 35/00069; G01N 35/00584;
G01N 35/00613; G01N 35/00712; G01N
35/0095; G01N 35/02; G01N 35/028;
G01N 35/1067; G01N 35/1083; G01N
35/109; G01N 5/04; G01N 1/2042; G01N
15/01; G01N 15/0205; G01N 15/04;
G01N 15/1012; G01N 15/12; G01N
15/147; G01N 2001/007; G01N
2001/045; G01N 2001/1062; G01N
2001/2007; G01N 2001/2255; G01N
2001/2833; G01N 2001/317; G01N
2001/382; G01N 2001/386; G01N
2001/4027; G01N 2001/4033; G01N
2015/0046; G01N 2015/012; G01N
2015/1022; G01N 2015/1029; G01N
2015/1415; G01N 2015/142; G01N
2015/1486; G01N 2021/0342; G01N
2021/1765; G01N 2021/8578; G01N
2030/027; G01N 2030/042; G01N
2030/062; G01N 2030/202; G01N
2030/204; G01N 2030/342; G01N
2035/00089; G01N 2035/00108; G01N
2035/00396; G01N 2035/00445; G01N
2035/0412; G01N 2035/0413; G01N
2035/0498; G01N 2035/1051; G01N
21/031; G01N 21/17; G01N 21/1702;
G01N 21/274; G01N 21/31; G01N
21/3103; G01N 21/3518; G01N 21/39;
G01N 21/6486; G01N 21/67; G01N
21/78; G01N 21/94; G01N 2223/0745;
G01N 2223/60; G01N 2223/616; G01N
2291/02416; G01N 2291/02809; G01N
23/20008; G01N 23/2202; G01N 23/222;
G01N 25/56; G01N 27/00; G01N 27/28;
G01N 27/623; G01N 30/22; G01N
30/6017; G01N 33/0036; G01N 33/0037;
G01N 33/004; G01N 33/0044; G01N
33/0047; G01N 33/0054; G01N 33/03;
G01N 33/1806; G01N 33/1846; G01N
33/204; G01N 33/207; G01N 33/246;
G01N 33/521; G01N 33/5304; G01N
33/54346; G01N 33/56966; G01N
35/00722; G01N 37/00; G01N 5/00;
G01N 5/025

USPC .......................................................... 73/863

See application file for complete search history.

(56) References Cited

U.S. PATENT DOCUMENTS

| 2005/0069257 | A1 | 3/2005 | Bhagavatula et al. |
| 2007/0104417 | A1 | 5/2007 | Tanaka et al. |
| 2008/0193083 | A1 | 8/2008 | Nagai et al. |
| 2019/0383708 | A1* | 12/2019 | Iida ............... G01N 1/28 |
| 2020/0182770 | A1 | 6/2020 | Tokonami et al. |
| 2022/0226814 | A1* | 7/2022 | Iida ............... G01N 1/44 |
| 2023/0194413 | A1* | 6/2023 | Iida ............... G01N 21/59 |
| | | | 356/432 |

FOREIGN PATENT DOCUMENTS

| CN | 1856721 A | 11/2006 |
| CN | 101246241 A | 8/2008 |

(56) References Cited

FOREIGN PATENT DOCUMENTS

| | | | |
|---|---|---|---|
| GB | 2545443 A | 6/2017 | |
| JP | 2001-284732 A | 10/2001 | |
| JP | 2002-219700 A | 8/2002 | |
| JP | 2007-507007 A | 3/2007 | |
| JP | 2008-068222 A | 3/2008 | |
| JP | 2009-049030 A | 3/2009 | |
| JP | 2011-062607 A | 3/2011 | |
| JP | 2017-202446 A | 11/2017 | |
| JP | 2019-056724 A | 4/2019 | |
| WO | 2010001841 A1 | 1/2010 | |
| WO | 2017/195872 A1 | 11/2017 | |
| WO | 2017/213107 A1 | 12/2017 | |
| WO | 2018/159706 A1 | 9/2018 | |
| WO | WO-2020218346 A1 * | 10/2020 | ............... G01N 1/10 |
| WO | WO-2023038087 A1 * | 3/2023 | |

OTHER PUBLICATIONS

Office Action in CN202080030830.2, mailed Feb. 2, 2023, 5 pages.
Office Action in CN202080030830.2, mailed Aug. 3, 2022, 12 pages.

* cited by examiner

FIG.14
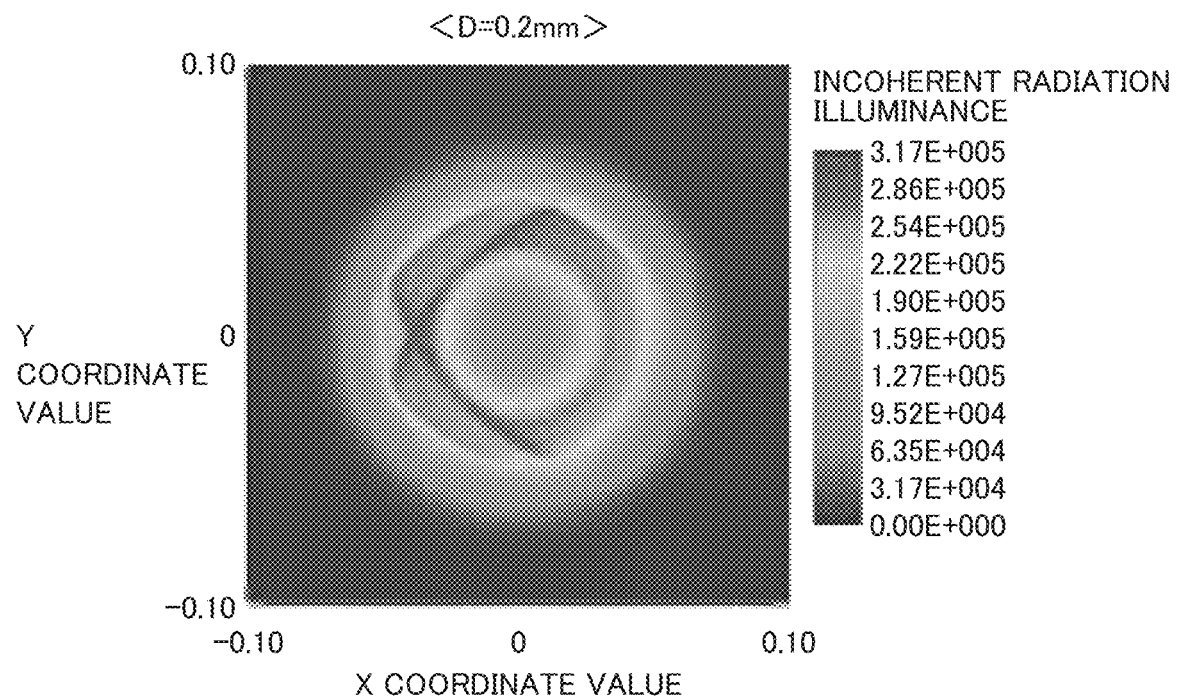
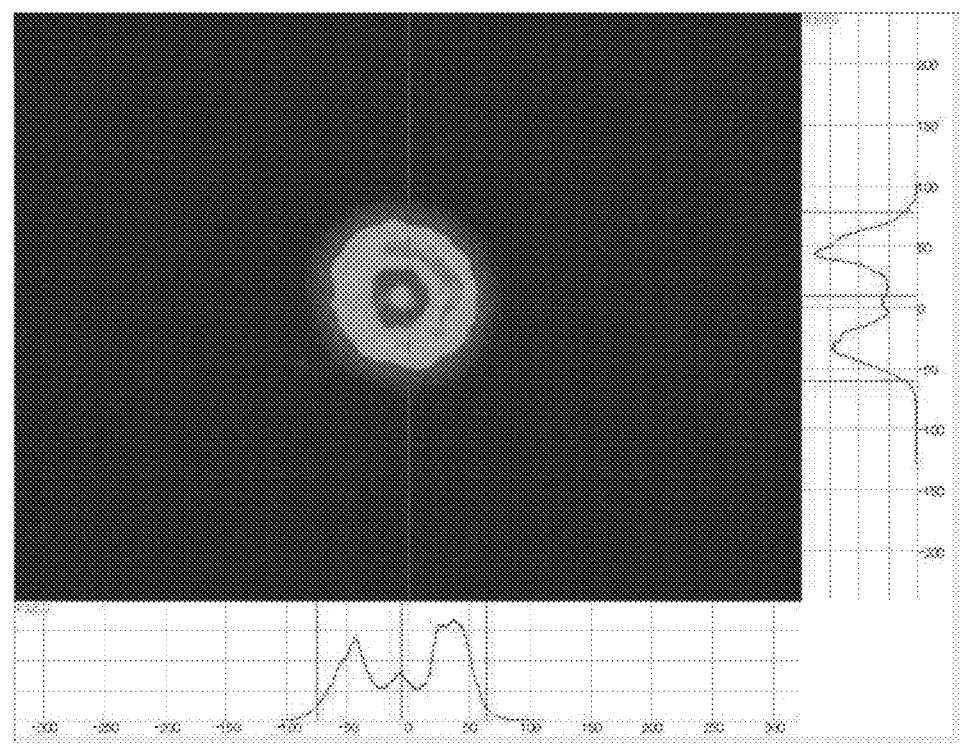

FIG.15
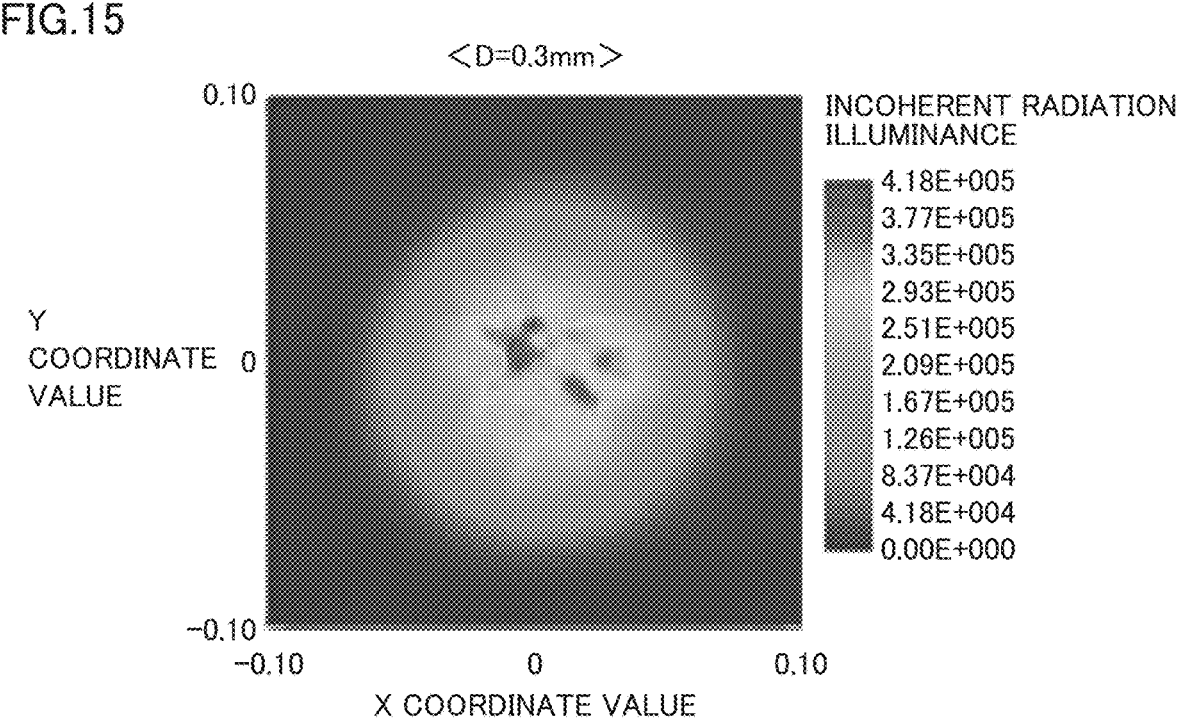
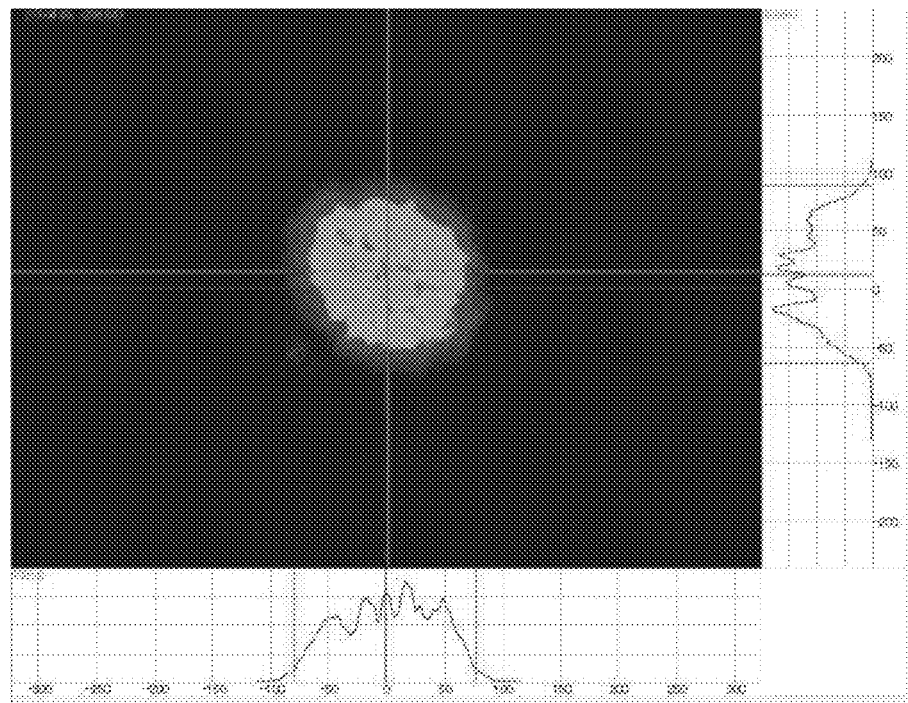

FIG.16
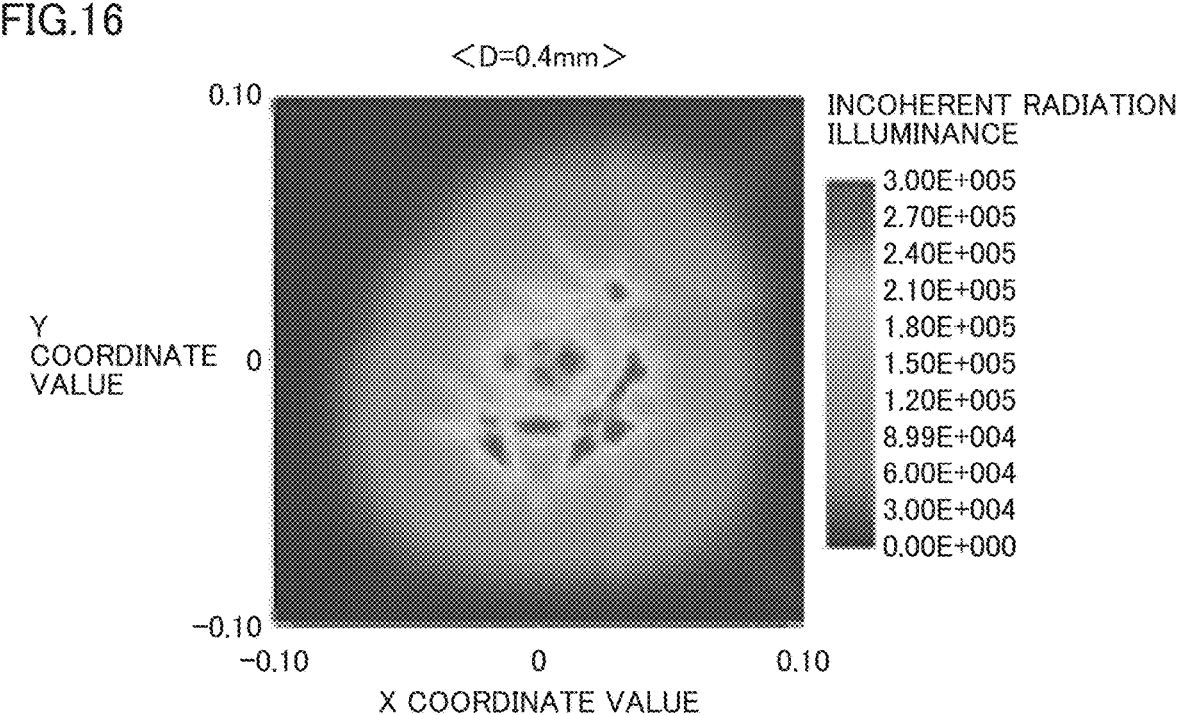
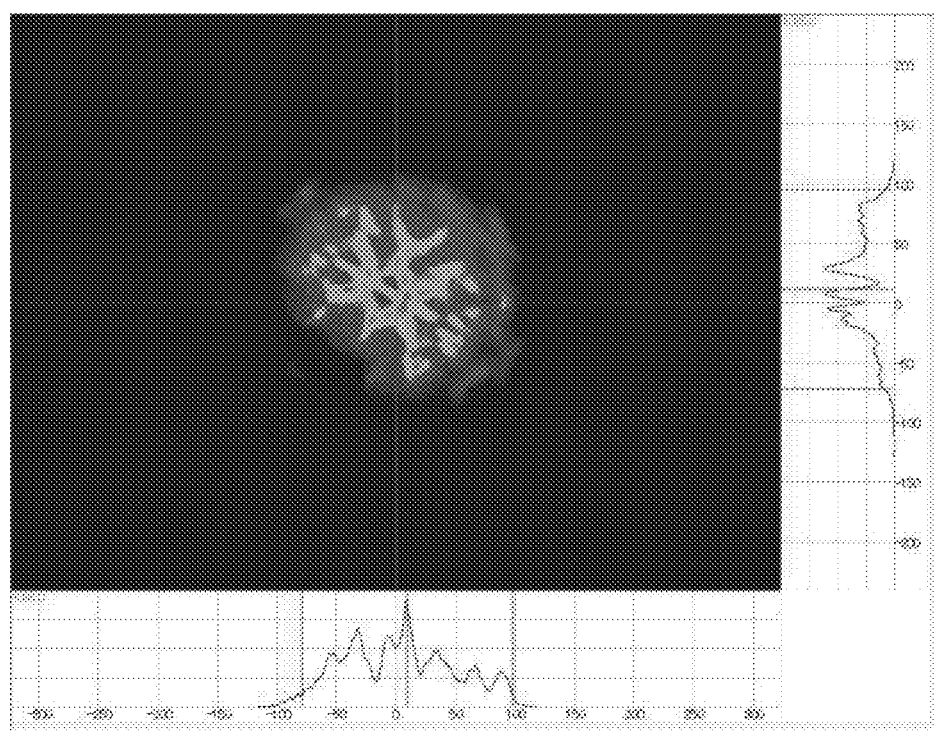

FIG.18
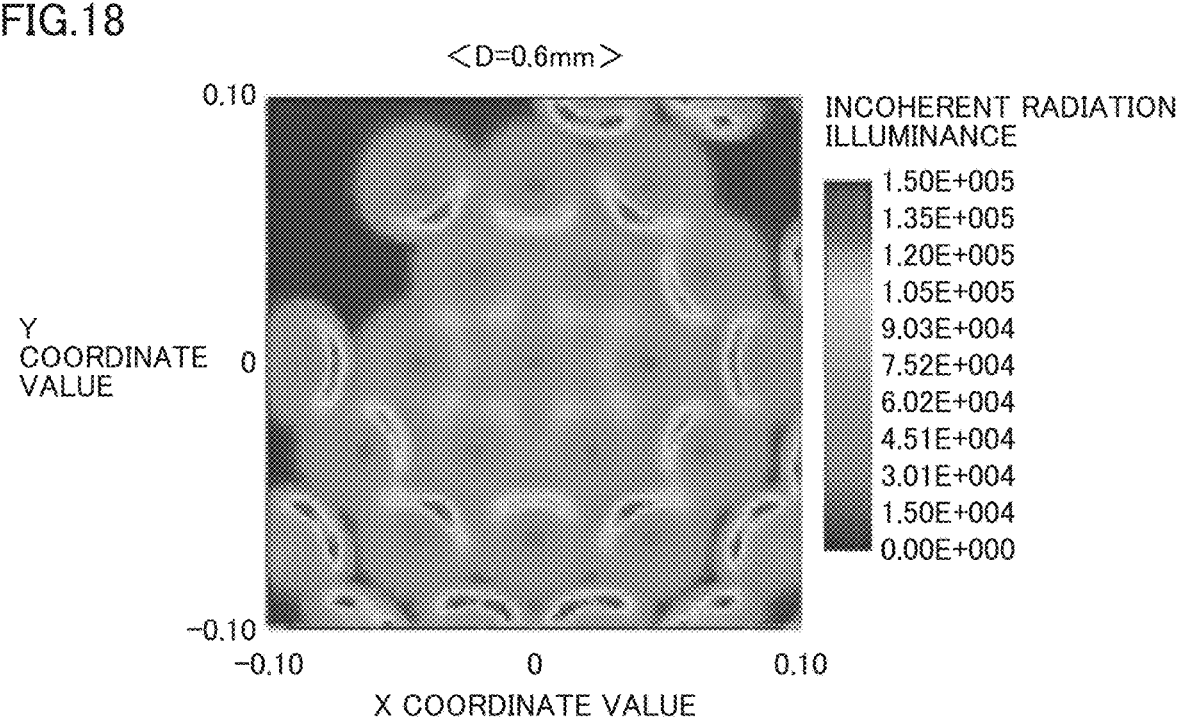
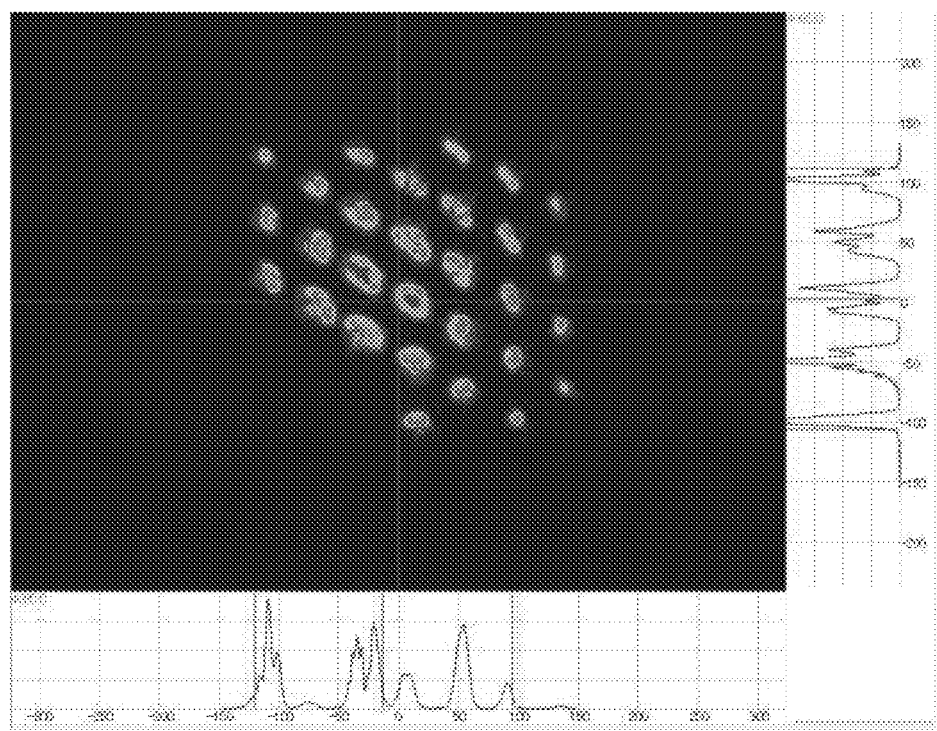

FIG.22
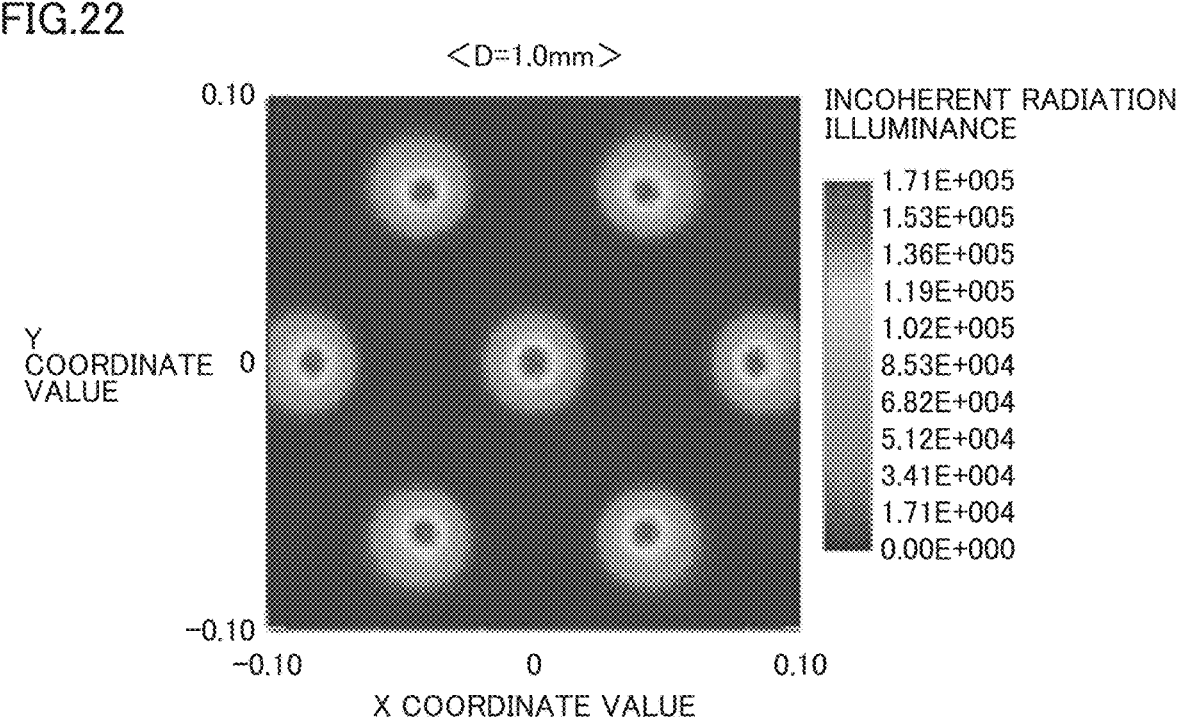
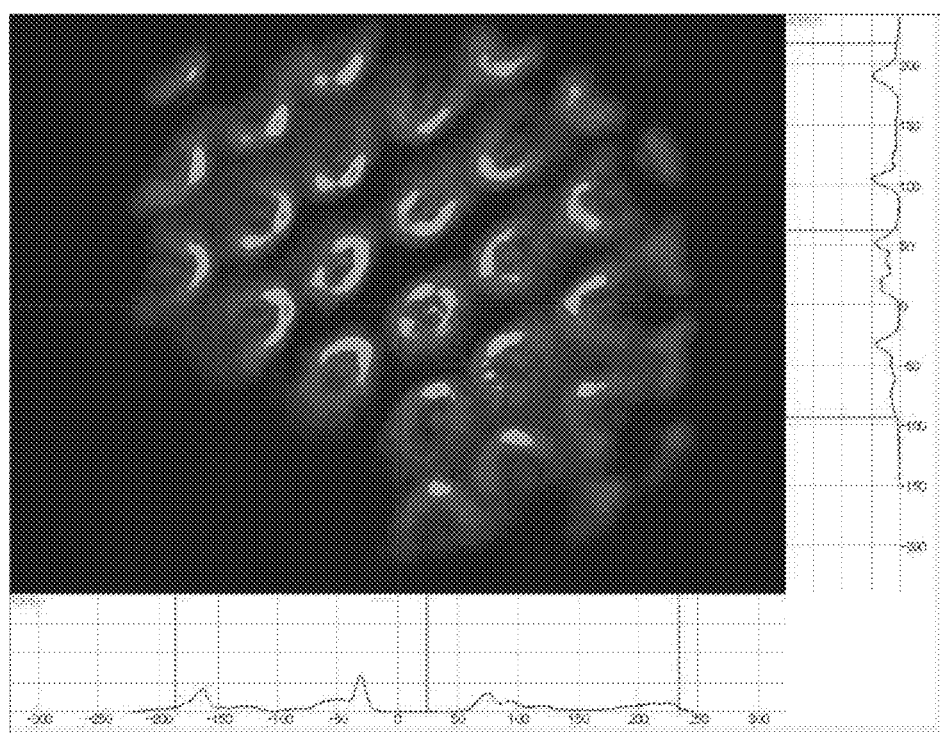

FIG.24
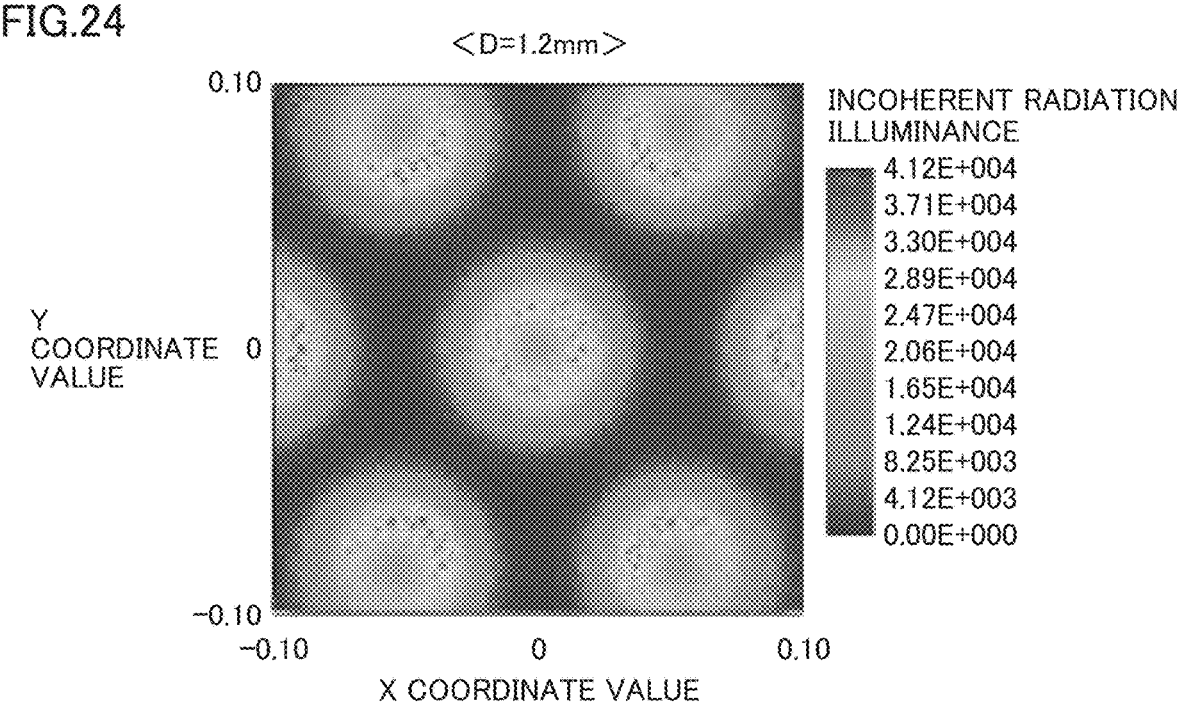
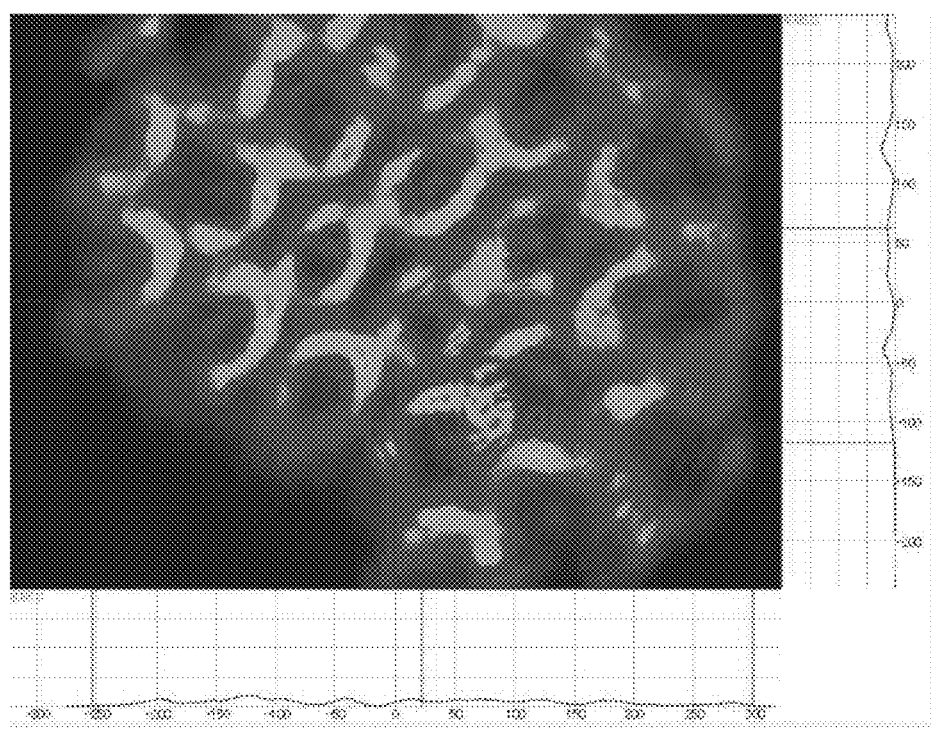

FIG.27
<SINGLE-POINT IRRADIATION MODE>
PERSPECTIVE IMAGE
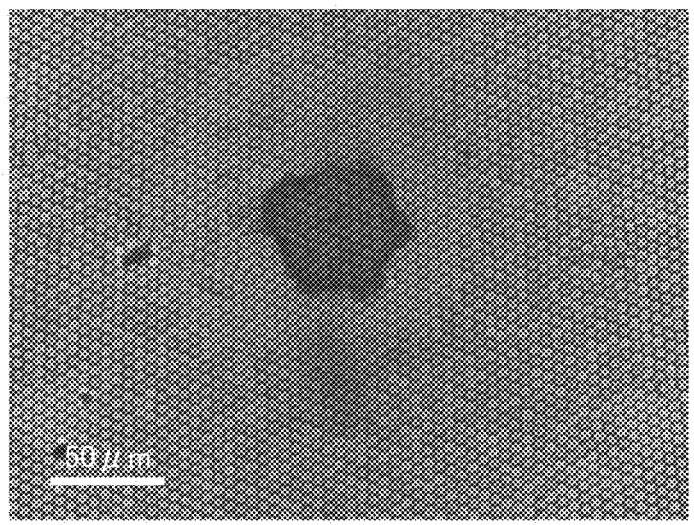
SYTO9 IMAGE
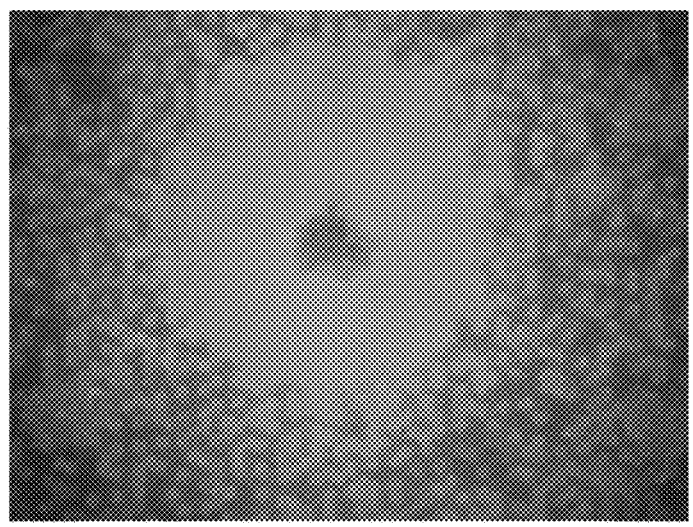
PI IMAGE
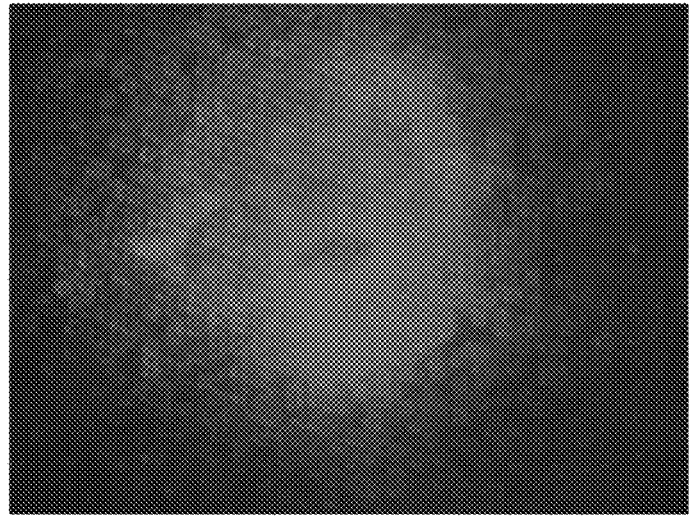

FIG.28
<MULTI-POINT IRRADIATION MODE>
PERSPECTIVE IMAGE
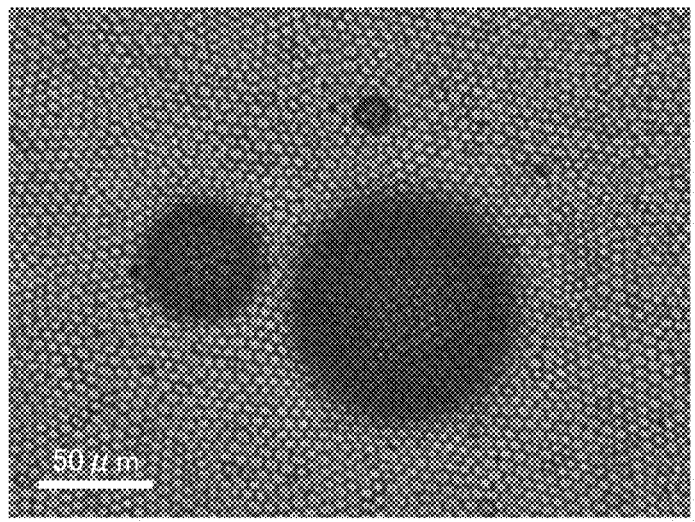
SYTO9 IMAGE
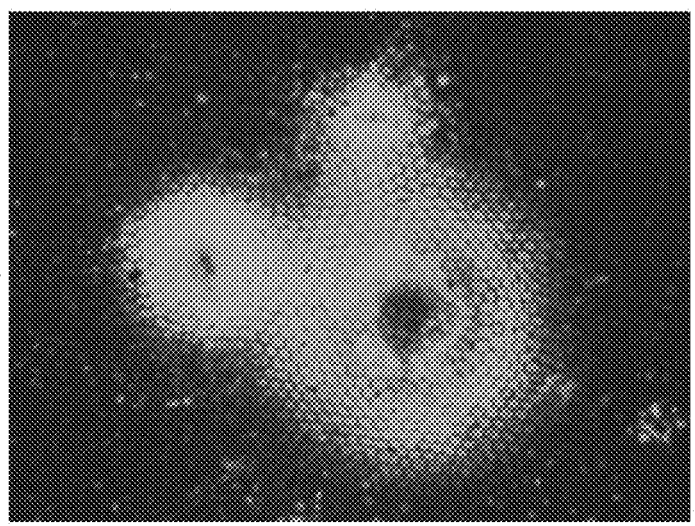
PI IMAGE
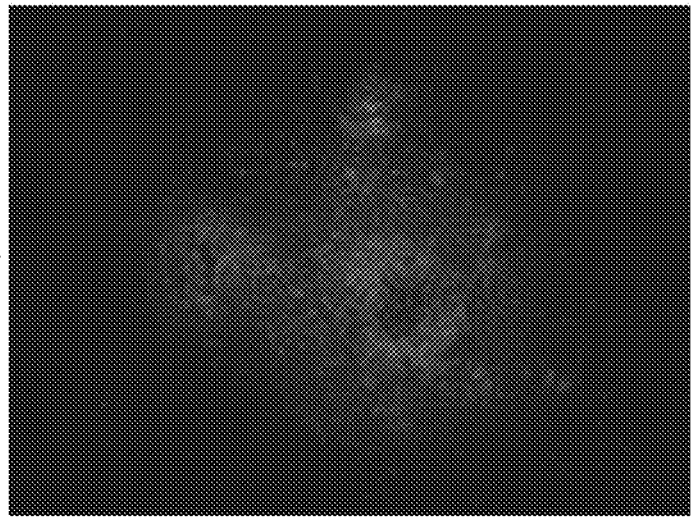

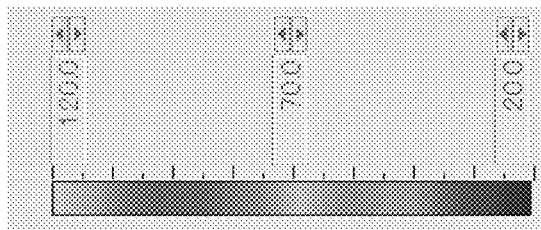
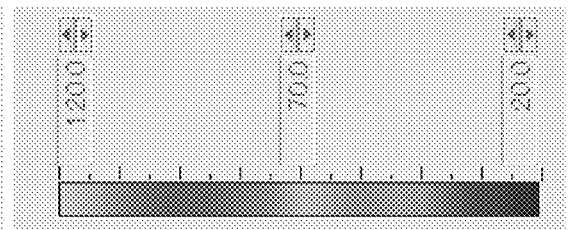
FIG.29

FIG.30
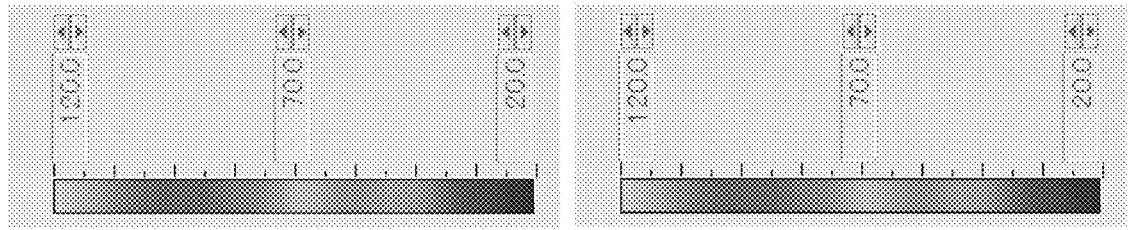
<HONEYCOMB COLLECTION KIT>
COMPARATIVE EXAMPLE
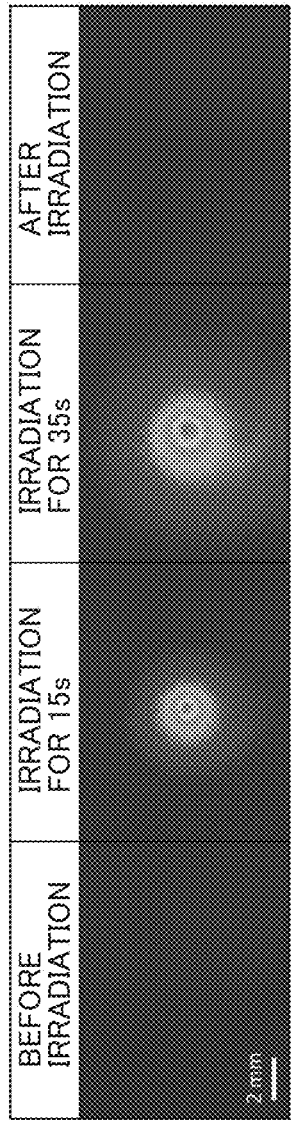
PRESENT EMBODIMENT
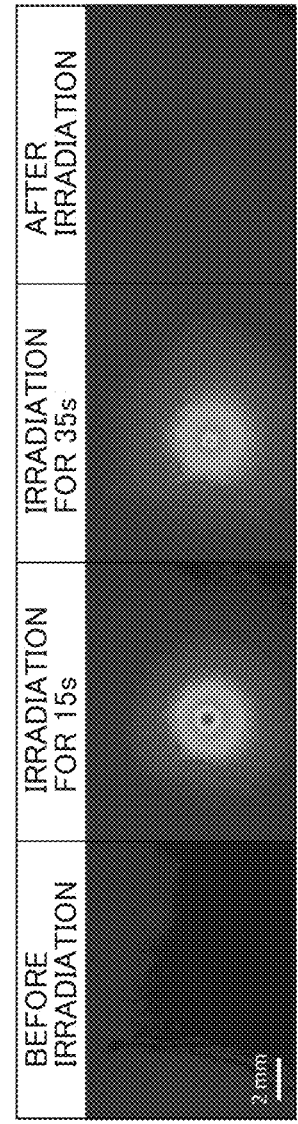

MICROSCOPIC OBJECT COLLECTION SYSTEM AND MICROSCOPIC OBJECT COLLECTION METHOD

TECHNICAL FIELD

The present disclosure relates to a microscopic object collection system and a microscopic object collection method, and more particularly to a technique for collecting a plurality of microscopic objects dispersed in a liquid.

BACKGROUND ART

A technique for collecting a plurality of microscopic objects (microparticles, cells, or microorganisms) dispersed in a liquid has been proposed. For example, Japanese Patent Laying-Open No. 2017-202446 (PTL 1) and WO2018/159706 (PTL 2) each disclose a technique for collecting a plurality of microscopic objects dispersed in a liquid by irradiation with light. As a photothermal conversion region where light is converted to heat is irradiated with light, the liquid in the vicinity of a position irradiated with light is locally heated. A microbubble is thus produced and convection is produced in the liquid. Then, the plurality of microscopic objects are carried by convection to the microbubble and collected in the vicinity of the position irradiated with light.

CITATION LIST

Patent Literature

PTL 1: Japanese Patent Laying-Open No. 2017-202446
PTL 2: WO2018/159706

SUMMARY OF INVENTION

Technical Problem

A collection system that collects a plurality of microscopic objects dispersed in a liquid by irradiation with light is required to collect more microscopic objects in a shorter period of time, that is, to collect microscopic objects more efficiently.

In order to highly efficiently collect microscopic objects, output of light emitted to the photothermal conversion region may be increased. With increase in optical output, however, temperature increase in the vicinity of the position irradiated with light becomes large. Some microscopic objects require suppression of thermal damage thereto. For example, since microorganisms are generally vulnerable to heat, they may be killed when a temperature excessively increases due to irradiation with light. Therefore, depending on microscopic objects, it may be desirable to suppress thermal damage thereto. On the other hand, some microscopic objects do not particularly require such consideration and optical output may simply be increased. Therefore, depending on a type or characteristics of microscopic objects, a user of the collection system can desirably make selection as to how the microscopic objects are to be collected.

The present disclosure was made to solve problems above, and an object thereof is to allow a user to select how a plurality of microscopic objects dispersed in a liquid are to be collected.

Solution to Problem (1) A microscopic object collection system according to one aspect of the present disclosure collects a plurality of microscopic objects dispersed in a liquid. The microscopic object collection system includes a holder configured to hold a substrate provided with a photothermal conversion region, a laser beam source including a plurality of light emission regions, the plurality of light emission regions emitting a plurality of laser beams, a condenser lens that condenses the plurality of laser beams to an identical focal point, an adjustment mechanism configured to adjust relative positional relation between the holder and the condenser lens, and a controller that controls the adjustment mechanism. The controller is configured to switch between a single-point irradiation mode and a multi-point irradiation mode, the single-point irradiation mode and the multi-point irradiation mode each being a mode for irradiating the photothermal conversion region with at least one of the plurality of laser beams. The single-point irradiation mode is a mode in which the adjustment mechanism is controlled such that the focal point of the plurality of laser beams falls on the photothermal conversion region. The multi-point irradiation mode is a mode in which the adjustment mechanism is controlled such that at least some of the plurality of laser beams pass through the photothermal conversion region while the focal point does not fall on the photothermal conversion region.

(2) In the multi-point irradiation mode, the controller sets an interval between the plurality of laser beams emitted to the photothermal conversion region by controlling the adjustment mechanism to adjust a distance between the condenser lens and the photothermal conversion region.

(3) The laser beam source is vertical cavity surface emitting laser.

(4) The condenser lens includes a graded-index optical fiber and a plano convex lens. The optical fiber includes one end that covers the plurality of light emission regions and the other end joined to a planar side of the plano convex lens.

(5) When the multi-point irradiation mode is selected under a condition that the liquid is prepared on the photothermal conversion region, the controller controls the adjustment mechanism to produce convection over the photothermal conversion region toward (i) a plurality of air bubbles and (ii) a gap between a plurality of air bubbles by emission of the plurality of laser beams and to thereby collect the plurality of microscopic objects in the gap.

(6) In a microscopic object collection method according to another aspect of the present disclosure, a plurality of microscopic objects dispersed in a liquid are collected. The microscopic object collection method includes first to fourth steps. The first step is a step of preparing the liquid on a photothermal conversion region provided in a substrate. The second step is a step of adjusting relative positional relation between a condenser lens that condenses a plurality of laser beams to an identical focal point and the photothermal conversion region. The adjusting relative positional relation (the second step) includes selectively setting a first state and a second state. The first state is a state in which the relative positional relation is adjusted such that the focal point of the plurality of laser beams falls on the photothermal conversion region. The second state is a state in which the relative positional relation is adjusted such that at least some of the plurality of laser beams pass through the photothermal conversion region while the focal point does not fall on the photothermal conversion region. The third step is a step of producing convection over the photothermal conversion region toward (i) a plurality of air bubbles and (ii) a gap between a plurality of air bubbles by emission of the plurality of laser beams when the second state is selected. The fourth step is a step of collecting the plurality of microscopic objects in the gap.

(7) In the substrate, a plurality of pores in which the plurality of microscopic objects are caught and a plurality of partition walls each serving as a partition between adjacent pores of the plurality of pores are provided. The photothermal conversion region is provided to cover at least one of the plurality of pores and the plurality of partition walls.

Advantageous Effects of Invention

According to the present disclosure, a user can select how a plurality of microscopic objects dispersed in a liquid are to be collected.

BRIEF DESCRIPTION OF DRAWINGS

FIG. 14 is a diagram showing a result of optical simulation at an interval between a plurality of laser beams and a result of actual measurement in the vicinity of a laser spot that correspond to an example where an irradiation distance D is set to 0.2 mm.

FIG. 15 is a diagram showing a result of optical simulation at an interval between a plurality of laser beams and a result of actual measurement in the vicinity of a laser spot that correspond to an example where irradiation distance D is set to 0.3 mm.

FIG. 16 is a diagram showing a result of optical simulation at an interval between a plurality of laser beams and a result of actual measurement in the vicinity of a laser spot that correspond to an example where irradiation distance D is set to 0.4 mm.

FIG. 18 is a diagram showing a result of optical simulation at an interval between a plurality of laser beams and a result of actual measurement in the vicinity of a laser spot that correspond to an example where irradiation distance D is set to 0.6 mm.

FIG. 22 is a diagram showing a result of optical simulation at an interval between a plurality of laser beams and a result of actual measurement in the vicinity of a laser spot that correspond to an example where irradiation distance D is set to 1.0 mm.

FIG. 24 is a diagram showing a result of optical simulation at an interval between a plurality of laser beams and a result of actual measurement in the vicinity of a laser spot that correspond to an example where irradiation distance D is set to 1.2 mm.

FIG. 27 is a diagram showing a result of observation of the honeycomb collection kit after single-point irradiation.

FIG. 28 is a diagram showing a result of observation of the honeycomb collection kit after multi-point irradiation.

FIG. 29 is a diagram showing a result of measurement of temperature increase by irradiation of the flat-plate collection kit with light.

FIG. 30 is a diagram showing a result of measurement of temperature increase by irradiation of the honeycomb collection kit with light.

DESCRIPTION OF EMBODIMENTS

Figure 1:
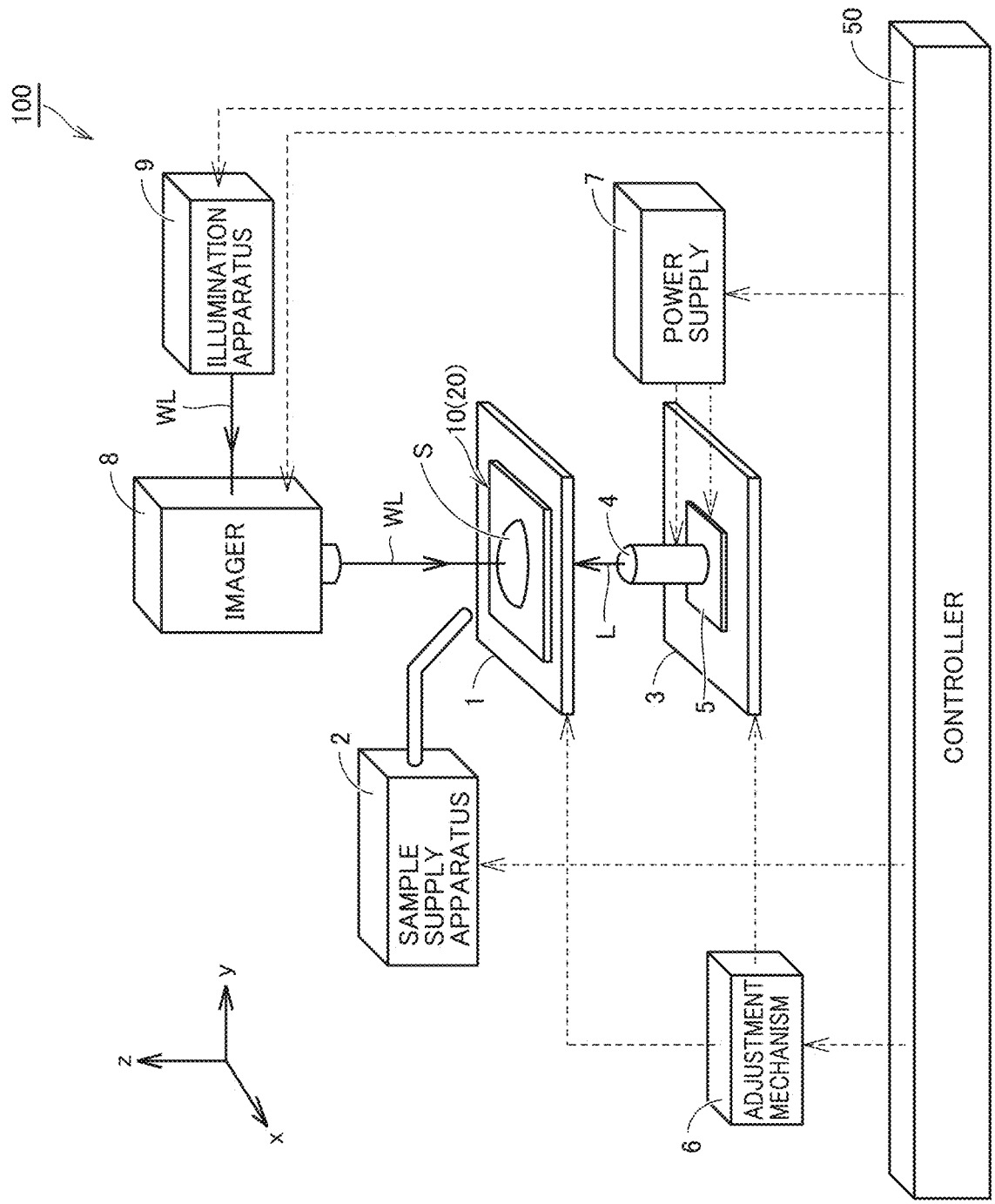
FIG. 1 is a diagram schematically showing an overall configuration of a microscopic object collection system according to the present embodiment.

In the present disclosure, a "nanometer order" includes a range from 1 nm to 1000 nm (=1 µm). A "micrometer order" includes a range from 1 µm to 1000 µm (=1 mm). Therefore, a "range from the nanometer order to the micrometer order" includes a range from 1 nm to 1000 µm. The "range from the nanometer order to the micrometer order" may typically represent a range from several nanometers to several hundred micrometers, preferably a range from 100 nm to 100 µm, and more preferably a range from 1 µm to several ten micrometers.

In the present disclosure, the term "microscopic object" means an object having a size within the range from the nanometer order to the micrometer order. A shape of the microscopic object is not particularly limited, and it may be, for example, in a spherical shape, a shape of an oval sphere, or a rod shape (a pole shape). When the microscopic object is in the shape of the oval sphere, at least one of a length in a direction of a major axis and a length in a direction of a minor axis of the oval sphere should only be within the range from the nanometer order to the micrometer order. When the microscopic object is in the rod shape, at least one of a width and a length of the rod should only be within the range from the nanometer order to the micrometer order.

Examples of microscopic objects include a metal nanoparticle, a metal nanoparticle assembly, a metal nanoparticle assembly structure body, a semiconductor nanoparticle, an organic nanoparticle, a resin bead, and a particulate matter (PM). The "metal nanoparticle" refers to a metal particle having a size of the nanometer order. The "metal nanoparticle assembly" refers to an assembly formed by aggregation of a plurality of metal nanoparticles. The "metal nanoparticle assembly structure body" refers, for example, to a structure body in which a plurality of metal nanoparticles are fixed to a surface of a substrate (a resin bead etc.) with an interactive site being interposed and arranged at intervals not larger than a diameter of each metal nanoparticle with gaps being interposed thereamong. The "semiconductor nanoparticle" refers to a semiconductor particle having a size of the nanometer order. The "organic nanoparticle" refers to a particle composed of an organic compound and having a size of the nanometer order. The "resin bead" refers to a particle composed of a resin and having a size within the range from the nanometer order to the micrometer order. The "PM" refers to a particulate substance having a size of the micrometer order. Examples of the PM include PM2.5 and a suspended particulate matter (SPM).

The microscopic object may be a biologically originated substance (a biological substance). More specifically, the microscopic object may include cells, microorganisms (bacteria, fungi, etc.), a biopolymer (protein, nucleic acid, lipid, polysaccharide, etc.), an antigen (allergen etc.), and a virus.

In the present disclosure, the term "honeycomb" means such a shape that a plurality of regular hexagons are disposed two-dimensionally in hexagonal lattices (like a honeycomb). Pores are provided in each of the plurality of regular hexagons. Each pore has an opening within the range from the nanometer order to the micrometer order. The pore may be a through hole or a non-through hole. A shape of the pore is not particularly limited, and the shape may include any shape such as a columnar shape, a prismatic shape, and a spherical shape except for a shape of a true sphere (for example, a hemispherical shape or a shape of a semielliptical sphere). A structure body with a structure in which a plurality of pores are disposed like a honeycomb is referred to as a "honeycomb structure body."

The term "microbubble" in the present disclosure means an air bubble of the micrometer order.

An embodiment of the present disclosure will be described below in detail with reference to the drawings. The same or corresponding elements in the drawings have the same reference characters allotted and description thereof will not be repeated.

Embodiment

In the present embodiment, resin beads or bacteria are adopted as an exemplary form of microscopic objects. Polystyrene is adopted as a material for the resin beads. The material for the resin beads is not limited thereto, and acrylic, polyolefin, polyethylene, or polypropylene may be adopted as the material. *Pseudomonas aeruginosa* is employed as bacteria. *Pseudomonas aeruginosa* is bacillus. *Pseudomonas aeruginosa* typically has a major axis having a length of approximately 2 µm and a short axis having a length of approximately 0.5 µm. *Pseudomonas aeruginosa* is gram-negative bacteria.

An x direction and a y direction represent a horizontal direction below. The x direction and the y direction are orthogonal to each other. A z direction represents a vertical direction. An orientation of the gravity is downward in the z direction. An upward direction in the z direction may be abbreviated as upward and a downward direction in the z direction may be abbreviated as downward.

In the present embodiment, two types of collection kits used for collection of microscopic objects are prepared. Though a detailed configuration of the collection kits will be described with reference to FIGS. 6 to 9, one of them is denoted as a "flat collection kit 10" and the other is denoted as a "honeycomb collection kit 20."

Configuration of Collection System

FIG. 1 is a diagram schematically showing an overall configuration of a microscopic object collection system 100 according to the present embodiment. Referring to FIG. 1, collection system 100 includes a sample stage 1, a sample supply apparatus 2, a light source stage 3, a laser module 4, a cooling apparatus 5, an adjustment mechanism 6, a power supply 7, an imager 8, an illumination apparatus 9, and a controller 50. Though an example using flat collection kit 10 will be described below, honeycomb collection kit 20 may be used instead of flat collection kit 10.

Sample stage 1 is an XYZ-axis stage and configured to be movable in the x direction, the y direction, and the z direction. Sample stage 1 holds flat collection kit 10. A sample S is dropped onto flat collection kit 10. Sample stage 1 corresponds to the "holder" according to the present disclosure.

Sample supply apparatus 2 supplies liquid sample S onto flat collection kit 10 in response to an instruction from controller 50. For example, a dispenser can be employed as sample supply apparatus 2.

Light source stage 3 is an XYZ-axis stage and configured to be movable in the x direction, the y direction, and the z direction. Light source stage 3 holds laser module 4 and cooling apparatus 5.

Laser module 4 is a semiconductor laser module (laser beam source), and emits a large number of laser beams L in response to an instruction from controller 50. A wavelength of laser beams L is within a near infrared region in this example, and it is, for example, 850 nm. A configuration of laser module 4 will be described in detail with reference to FIGS. 2 to 5.

Cooling apparatus 5 cools laser module 4. Cooling apparatus 5 can be compact by employing a Peltier element (not shown) as cooling apparatus 5.

Adjustment mechanism 6 is configured to adjust a position of sample stage 1 in the x direction, the y direction, and the z direction and to adjust a position of light source stage 3 in the x direction, the y direction, and the z direction, in response to an instruction from controller 50. In an example which will be described below, in determining a position to be irradiated with light, a horizontal position (a position in the x direction and the y direction) of sample stage 1 is adjusted and a height (a position in the z direction) of light source stage 3 is adjusted. Relative positional relation between flat collection kit 10 mounted on sample stage 1 and laser module 4 provided on light source stage 3 is thus adjusted.

The configuration of adjustment mechanism 6 is not particularly limited so long as relative positional relation between flat collection kit 10 and laser module 4 can be adjusted. Adjustment mechanism 6 may adjust, for example, the position of flat collection kit 10 with respect to fixed laser module 4 or may adjust the position of laser module 4 with respect to fixed flat collection kit 10.

Power supply 7 supplies a current for driving laser module 4. Power supply 7 supplies electric power for driving cooling apparatus 5.

Imager 8 takes an image of sample S on flat collection kit 10 in response to an instruction from controller 50 and provides the taken image to controller 50. A video camera including charge coupled device (CCD) image sensors or complementary metal oxide semiconductor (CMOS) image sensors is employed as imager 8.

Illumination apparatus 9 emits white light WL for irradiating sample S on flat collection kit 10 in response to an instruction from controller 50. In one example, a halogen lamp can be employed as illumination apparatus 9. White light WL emitted from illumination apparatus 9 is guided to imager 8, for example, through optical fibers, and emitted from imager 8 toward a portion of imaging. Imager 8 and illumination apparatus 9 are merely devices for taking an image of a state of sample S and they are not constituent elements essential for collection of microscopic objects by collection system 100.

Controller 50 controls each device (sample supply apparatus 2, adjustment mechanism 6, power supply 7, imager 8, and illumination apparatus 9) included in collection system 100. Controller 50 is implemented by a microcomputer including a processor such as a central processing unit (CPU), a memory such as a read only memory (ROM) and a random access memory (RAM), and an input and output port (none of which is shown).

Figure 2:
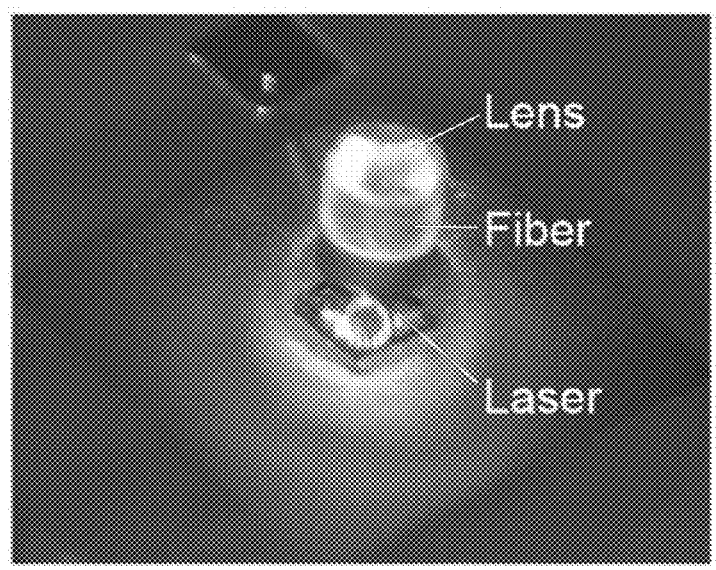
FIG. 2 is a diagram showing a perspective image of a laser module.
Figure 3:
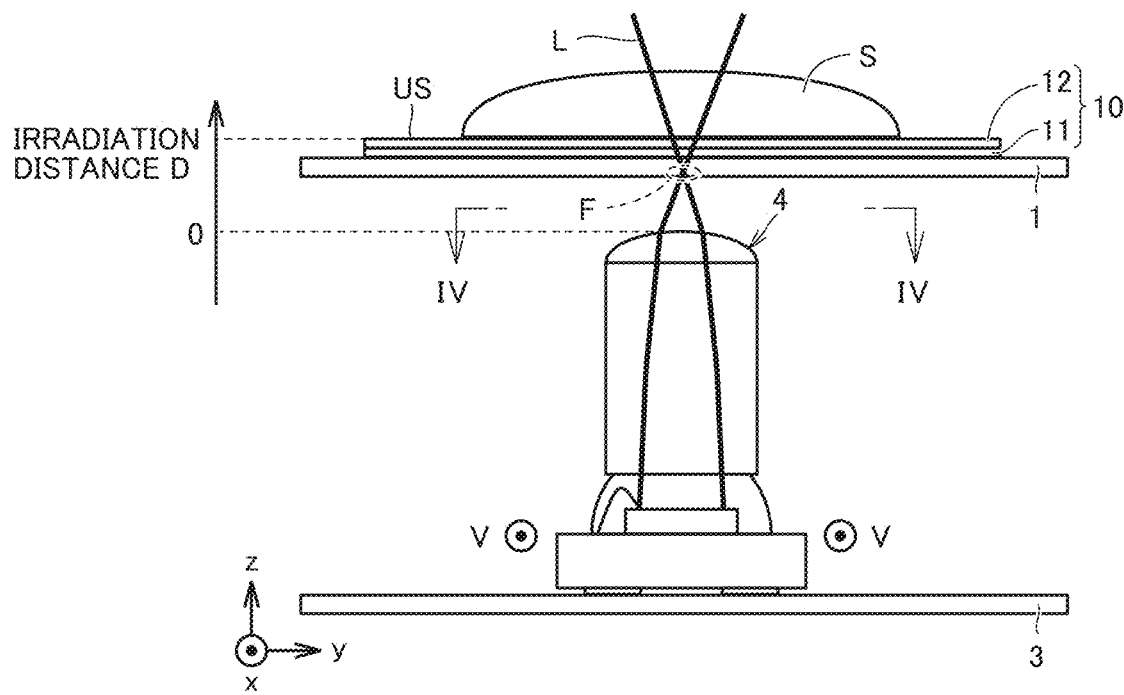
FIG. 3 is a diagram schematically showing a configuration of the laser module.

FIG. 2 is a diagram showing a perspective image of laser module 4. FIG. 3 is a diagram schematically showing a configuration of laser module 4. Referring to FIGS. 2 and 3, laser module 4 is provided on light source stage 3 and arranged below sample stage 1. Flat collection kit 10 is provided on sample stage 1. Flat collection kit 10 on sample stage 1 is irradiated with a large number of laser beams L (a plurality of laser beams L) emitted upward from laser module 4. Cooling apparatus 5 is not shown in FIG. 3 and FIG. 10 which will be described later.

Figure 4:
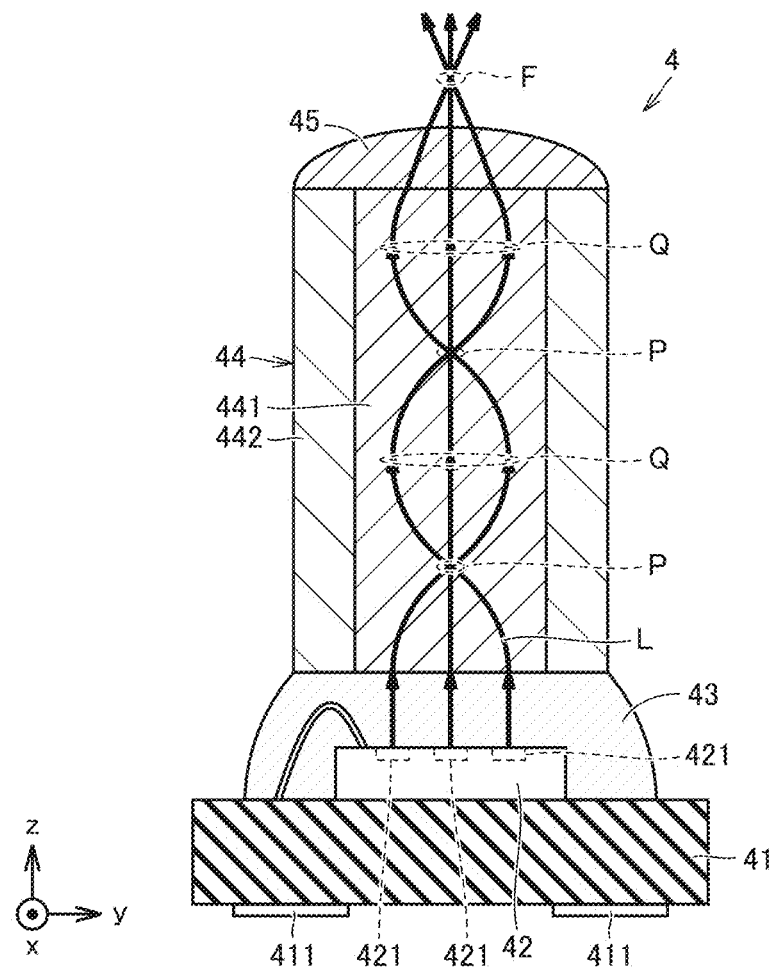
FIG. 4 is a cross-sectional view of the laser module along the line IV-IV in FIG. 3.
Figure 5:
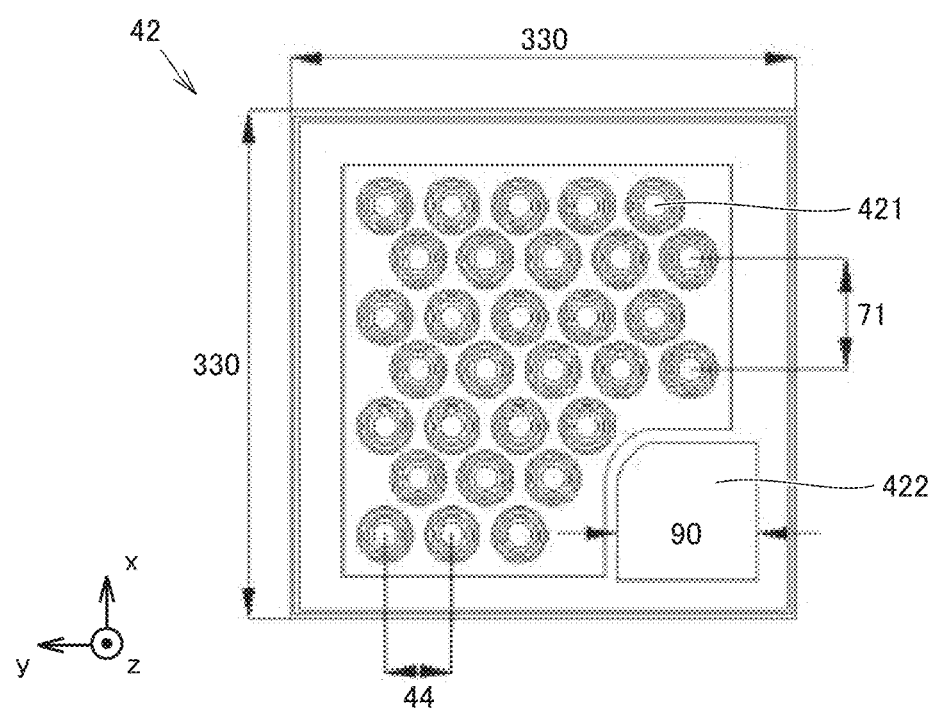
FIG. 5 is a cross-sectional view of the laser module along the line V-V in FIG. 3.

FIG. 4 is a cross-sectional view of laser module 4 along the line IV-IV in FIG. 3. FIG. 5 is a cross-sectional view of laser module 4 along the line V-V in FIG. 3. Referring to FIG. 4, laser module 4 includes a substrate 41, a surface emission element 42, a joint member 43, an optical waveguide 44, and a lens 45.

Substrate 41 is a flat plate formed of an insulating material, and it is, for example, a printed circuit board or a ceramic substrate. Surface emission element 42 is mounted on a surface of substrate 41. A part of an electrode 411 is formed on a rear surface of substrate 41. Electrode 411 is electrically connected to surface emission element 42, for example, by wire bonding. A drive current is supplied to surface emission element 42 from power supply 7 (see FIG. 1) through electrode 411.

Referring to FIG. 5, surface emission element 42 is array-type vertical cavity surface emitting laser (VCSEL). Surface emission element 42 includes a plurality of (thirty in this example) light emission regions 421 and an electrode pad 422. The plurality of light emission regions 421 are disposed in an array. All light emission regions 421 simultaneously emit light and each emits laser beam L. A plurality of emitted laser beams L go out in a direction perpendicular to a surface of surface emission element 42 (upward in the z direction). A numerical value in FIG. 5 represents a dimension (unit of μm) of each constituent element.

Referring back to FIG. 4, for example, an adhesive is employed as joint member 43, and joins optical waveguide 44 onto surface emission element 42. Joint member 43 is made of a material transparent to light (near infrared light in this example) emitted from surface emission element 42.

Optical waveguide 44 condenses a plurality of laser beams L emitted from surface emission element 42. A material for optical waveguide 44 is transparent to light emitted from surface emission element 42, and for example, a resin or glass is employed as the material. Optical waveguide 44 includes a core 441 and a clad 442.

Core 441 is in a columnar shape. An incident end (corresponding to "one end" according to the present disclosure) of core 441 is formed to cover all light emission regions 421 such that all laser beams L emitted from surface emission element 42 are incident thereto. Clad 442 is in a cylindrical shape. Clad 442 is formed to cover a side surface of core 441.

Lens 45 is a plano convex lens and includes a plane and a convex surface. The plane of lens 45 is joined to an emission end (corresponding to "the other end" according to the present disclosure) of optical waveguide 44. The convex surface of lens 45 protrudes in a direction of emission of light from a laser emission portion of laser module 4.

A path of propagation of laser beams L in laser module 4 configured as above will be described. Optical waveguide 44 is a graded-index (GI) optical fiber. Therefore, an index of refraction of core 441 of optical waveguide 44 is highest at the center in a radial direction of core 441 and smoothly lowers toward radially outside. Laser beams L that propagates through the inside of core 441 have a plurality of modes different from each other in propagation distance. Light in a lower-order mode advances through the center of the core and light in a higher-order mode advances as being displaced from the center of the core. Though a propagation distance of light in the lower-order mode is short, a speed of propagation of light in the lower-order mode is relatively low due to the high index of refraction at the center of the core. In contrast, light in the higher-order mode is long in propagation distance whereas it is relatively high in propagation speed. A distribution of the index of refraction of core 441 is designed such that a difference in propagation time period between the modes is sufficiently small.

The plurality of laser beams L that propagate through the inside of core 441 having such a distribution of the index of refraction form a node P and an antinode Q. Positions of node P and antinode Q may vary depending on a wavelength of laser beams L. In connection with a direction in which laser beams L travel, a length of optical waveguide 44 is determined such that the emission end of optical waveguide 44 is not located at a position somewhere between node P and antinode Q. In other words, the length of optical waveguide 44 is determined such that the emission end of optical waveguide 44 is located somewhere between antinode Q and node P as shown in FIG. 4 or the emission end of optical waveguide 44 coincides with antinode Q. Consequently, the plurality of laser beams L that have propagated through optical waveguide 44 are emitted from the emission end of optical waveguide 44 with the tendency of being condensed. The plurality of emitted laser beams L are further condensed by lens 45 to form an identical focal point F.

Configuration of Collection Kit

Figure 6:
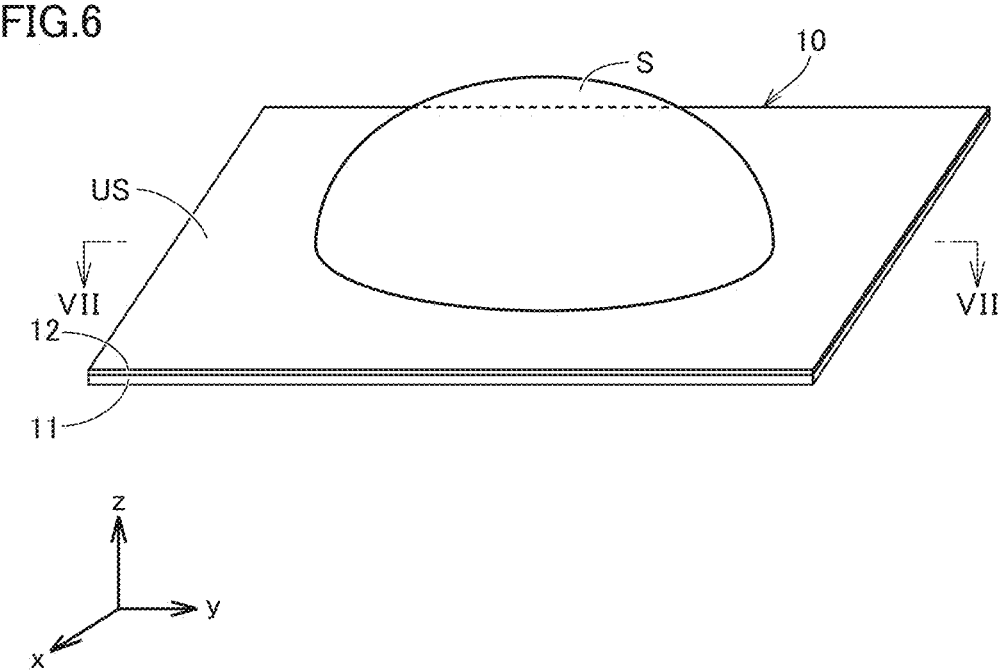
FIG. 6 is a perspective view schematically showing a configuration of a flat-plate collection kit.
Figure 7:
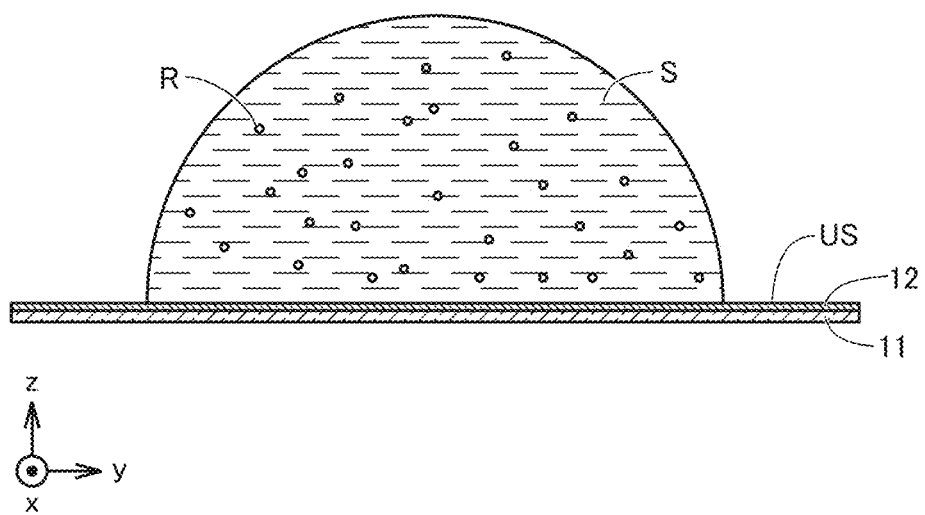
FIG. 7 is a cross-sectional view of the flat-plate collection kit along the line VII-VII in FIG. 6.

FIG. 6 is a perspective view schematically showing a configuration of flat collection kit 10. FIG. 7 is a cross-sectional view of flat collection kit 10 along the line VII-VII in FIG. 6.

Referring to FIGS. 6 and 7, flat collection kit 10 is in a shape of a flat plate. Sample S is dropped on an upper surface US in this shape of the flat plate.

Sample S is a liquid in which resin beads R are dispersed in an example shown in FIG. 7. Though a type of a liquid (dispersion medium) is not particularly limited, water is adopted as the liquid in this example. A non-ionic surfactant for expediting collection of resin beads R may be added to sample S (see PTL 2 for details of a function of the surfactant).

Flat collection kit 10 includes a substrate 11 and a thin film 12. Substrate 11 is formed of a material that does not affect photothermal conversion (which will be described later) of laser beams L by thin film 12 and is transparent to white light WL. Examples of such a material include quartz and silicon. In the present embodiment, a glass substrate (cover glass) is employed as substrate 11.

Thin film 12 absorbs laser beams L from laser module 4 and converts light energy into thermal energy. A material for thin film 12 is preferably high in photothermal conversion efficiency in a wavelength range (the near infrared range in the present embodiment) of laser beams L. In the present embodiment, a gold thin film having a thickness of the nanometer order (specifically, for example, 10 nm) is formed as thin film 12. The gold thin film can be formed by using a known method such as sputtering or electroless plating. Thin film 12 does not have to be formed on the entire surface of substrate 11 but should only be formed on at least a part of substrate 11.

When the gold thin film is formed as thin film 12, free electrons at a surface of the gold thin film form surface plasmons and are oscillated by laser beams L. Polarization thus occurs. Energy of this polarization is converted to energy of lattice vibration as a result of Coulomb interaction between free electrons and nuclei. Consequently, the gold thin film generates heat. This effect is also referred to as a "photothermal effect" below.

The material for thin film 12 is not limited to gold, and a metal element (for example, silver) other than gold or a metal nanoparticle assembly structure body (for example, a structure body containing gold nanoparticles or silver nanoparticles) that may achieve the photothermal effect may be applicable. Alternatively, the material for thin film 12 may be a material other than a metal high in light absorption factor in the wavelength range of laser beams L. Examples of such a material include a material close to a black body (for example, a carbon nanotube black body). A thickness of thin film 12 is determined in terms of design or experimentally, taking into account laser output as well as an absorption wavelength range and photothermal conversion efficiency of the material for thin film. A region where thin film 12 is formed corresponds to the "photothermal conversion region" according to the present disclosure.

Figure 8:
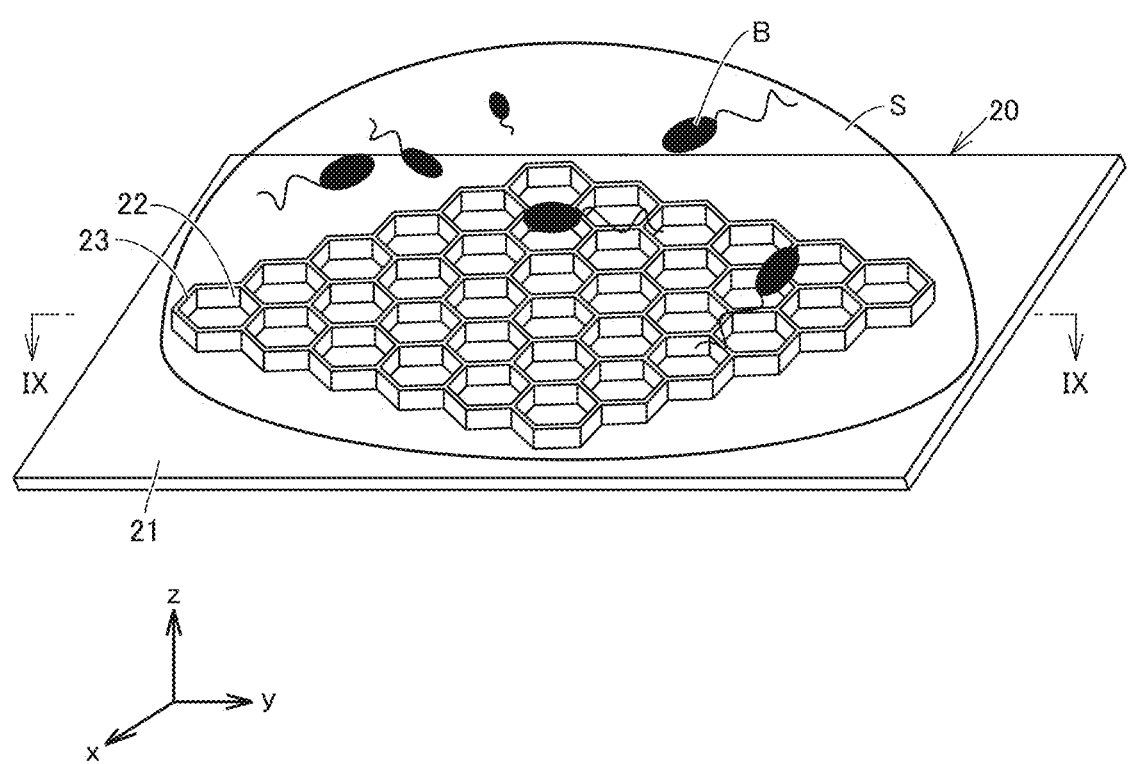
FIG. 8 is a perspective view schematically showing a configuration of a honeycomb collection kit.
Figure 9:
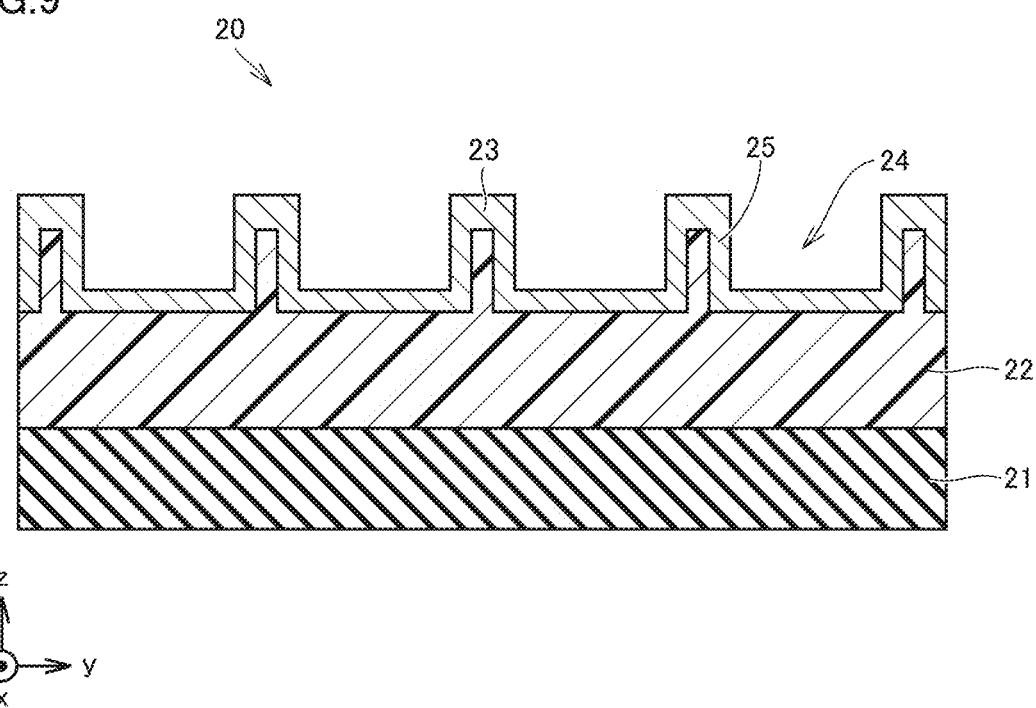
FIG. 9 is a cross-sectional view of the honeycomb collection kit along the line IX-IX in FIG. 8.

FIG. 8 is a perspective view schematically showing a configuration of honeycomb collection kit 20. FIG. 9 is a cross-sectional view of honeycomb collection kit 20 along the line IX-IX in FIG. 8. FIG. 9 does not show sample S.

Referring to FIGS. 8 and 9, honeycomb collection kit 20 includes a substrate 21, a honeycomb polymeric film 22, and a thin film 23.

For example, cover glass is employed as substrate 21. Honeycomb polymeric film 22 is a polymeric film on substrate 21 in which a honeycomb structure body is formed. A resin is employed as a material for honeycomb polymeric film 22. Thin film 23 is further formed on honeycomb polymeric film 22.

Thin film 23 is composed of a material that converts light energy into thermal energy by absorbing laser beams L, similarly to thin film 12 (see FIGS. 6 and 7) formed in flat collection kit 10. In the present embodiment, thin film 23 is a gold thin film having a thickness of the nanometer order (specifically, for example, from 40 nm to 50 nm). Thin film 23 has a honeycomb structure with the structure of honeycomb polymeric film 22 being reflected. Therefore, a plurality of pores 24 in which a plurality of microscopic objects are caught and a plurality of partition walls 25 each serving as a partition between adjacent pores of the plurality of pores 24 are formed in thin film 23 (see PTL 2 for a detailed configuration of honeycomb collection kit 20). Thin film 23 is provided to cover at least one of the plurality of pores 24 and upper portions of the plurality of partition walls 25.

A shape of flat collection kit 10 and honeycomb collection kit 20 is not limited to the shape of the flat plate. Flat collection kit 10 and honeycomb collection kit 20 may be a container in which an internal space for holding sample S is defined. Specifically, a columnar glass bottom dish (see PTL 2) can be employed as flat collection kit 10 or honeycomb collection kit 20. In this case, a bottom surface of the glass bottom dish corresponds to the "substrate" according to the present disclosure. The gold thin film can be formed on the bottom surface of the glass bottom dish.

Single-Point Irradiation Mode and Multi-Point Irradiation Mode

Referring again to FIG. 3, a distance from a tip end (the convex surface of lens 45) of laser module 4 to upper surface US (thin film 12) of flat collection kit 10 along the direction of emission (the z direction) of laser beams L is referred to as an "irradiation distance D" below. As described with reference to FIG. 1, adjustment mechanism 6 is configured to adjust the position of light source stage 3 in the z direction in response to an instruction from controller 50. Therefore, controller 50 can set irradiation distance D to any value by controlling adjustment mechanism 6.

Collection system 100 according to the present embodiment is configured to switch between a "single-point irradiation mode" and a "multi-point irradiation mode" by setting irradiation distance D. The single-point irradiation mode refers to a mode for irradiating sample S with single laser beam L. The multi-point irradiation mode refers to a mode for irradiating sample S with a large number of laser beams L. "Multi-point irradiation" means irradiation of at least two points.

Figure 10:
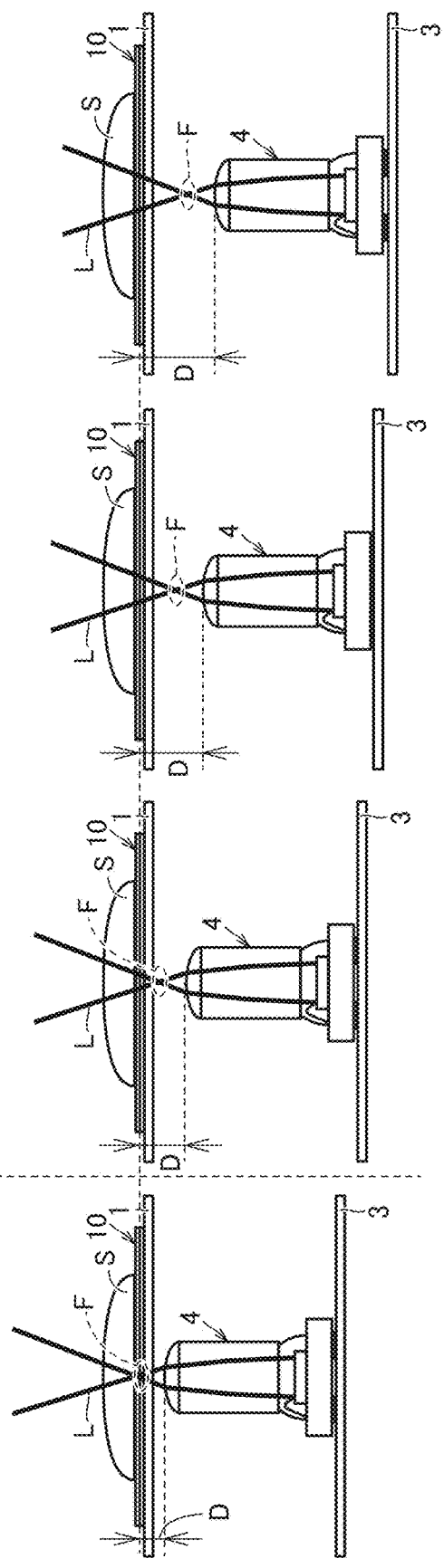
FIG. 10 is a diagram for illustrating a method of switching between a single-point irradiation mode and a multi-point irradiation mode.

FIG. 10 is a diagram for illustrating a method of switching between the single-point irradiation mode and the multi-point irradiation mode. Referring to FIGS. 3 and 10, a plurality of laser beams L emitted upward from the tip end of laser module 4 are separate from one another in the vicinity of lens 45, however, they intersect with one another thereabove to form focal point F. Then, the plurality of laser beams L are again separate from one another further above focal point F.

When controller 50 sets irradiation distance D such that a position of focal point F coincides with upper surface US of flat collection kit 10, flat collection kit 10 is irradiated with single laser beam L. In other words, single-point irradiation of flat collection kit 10 is realized (the single-point irradiation mode or the first state).

In contrast, when controller 50 sets irradiation distance D such that the position of focal point F is located below upper surface US of flat collection kit 10, flat collection kit 10 is irradiated with a plurality of laser beams L. In other words, multi-point irradiation of flat collection kit 10 is realized (the multi-point irradiation mode or the second state). Though not shown in this example, multi-point irradiation may be realized by setting of irradiation distance D by controller 50 such that the position of focal point F is located above upper surface US of flat collection kit 10.

An interval between the plurality of laser beams L at the position of upper surface US of flat collection kit 10 in the multi-point irradiation mode is referred to as a "spot interval." The spot interval is larger as the position of upper surface US of flat collection kit 10 is located further above focal point F. Therefore, controller 50 can also set the spot interval to a desired value by controlling adjustment mechanism 6 to adjust irradiation distance D.

Collection Flow

Figure 11:
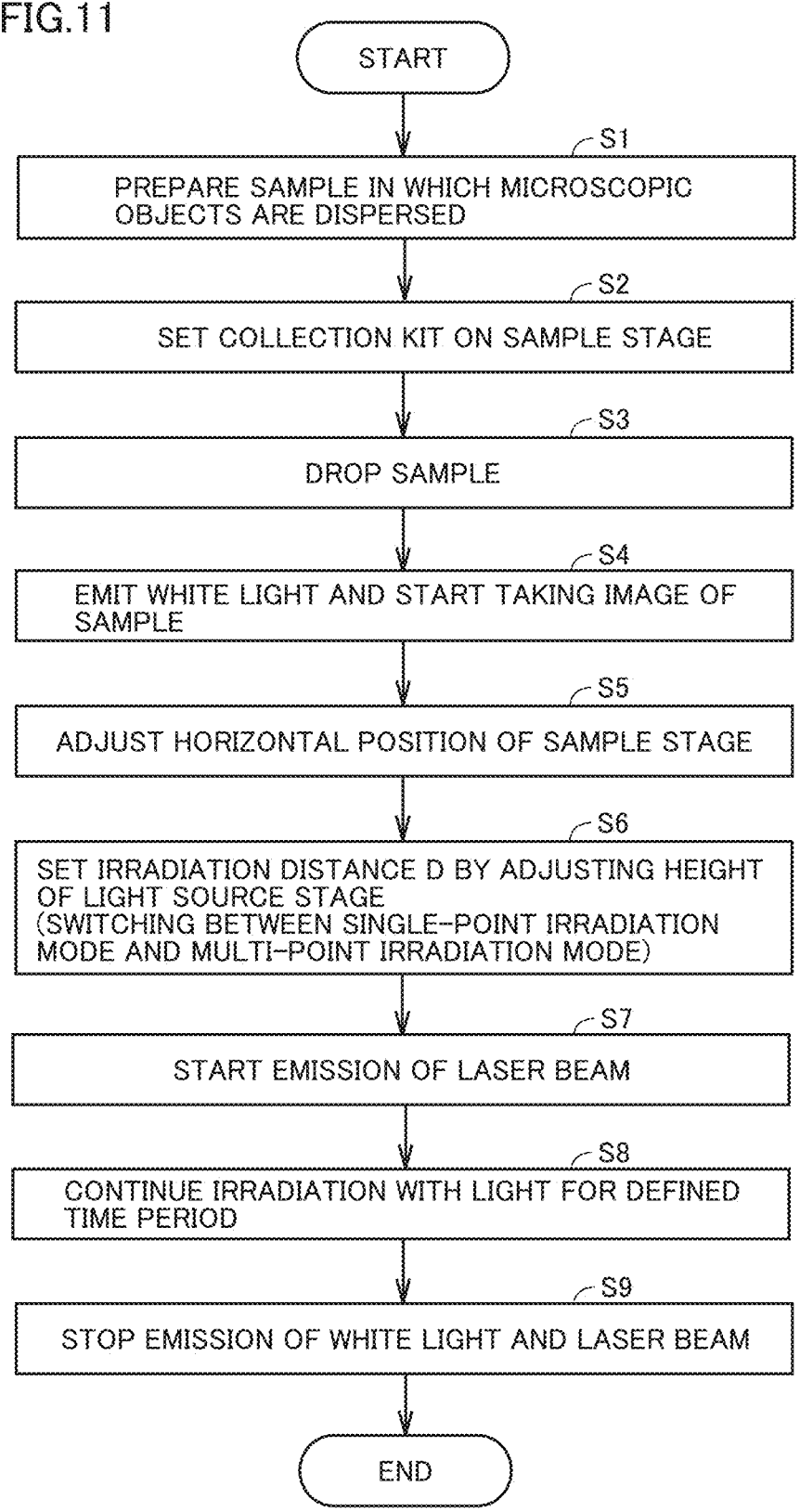
FIG. 11 is a flowchart showing a method of collecting microscopic objects in the present embodiment.

FIG. 11 is a flowchart showing a method of collecting microscopic objects (resin beads R or bacteria B) in the present embodiment. Though each step after step S3 is basically performed by software processing by controller 50 in this flowchart, a part or the entirety thereof may be performed by hardware (electric circuitry) made in controller 50.

Referring to FIG. 11, in step S1, sample S in which microscopic objects are dispersed is prepared. Prepared sample S is stored in sample supply apparatus 2.

In step S2, controller 50 has flat collection kit 10 set on sample stage 1. This processing can be realized, for example, by a substrate feed mechanism (not shown) provided in collection system 100.

In step S3, controller 50 controls sample supply apparatus 2 to drop an appropriate amount of sample S onto flat collection kit 10. An amount of dropped sample S may be, for example, a trace amount from several microliters to several hundred microliters or an amount larger than that.

In step S4, controller 50 controls illumination apparatus 9 to emit white light WL for irradiation of sample S. Controller 50 controls imager 8 to start taking an image of sample S. Processing in step S4 is processing for observing sample S and not essential for collection of resin beads R.

In step S5, controller 50 controls adjustment mechanism 6 to adjust a horizontal position of sample stage 1 such that an aimed position of sample S is irradiated with laser beams L. Specifically, controller 50 can obtain a horizontal position of sample S by extracting an outer geometrical pattern of sample S with the use of an image processing technique for pattern recognition from the image taken by imager 8. Then, controller 50 adjusts the horizontal position of light source stage 3 as appropriate from an initial position to thereby set a horizontal position of irradiation with laser beams L to an aimed position in sample S.

In step S6, controller 50 controls adjustment mechanism 6 to adjust the height of light source stage 3 such that irradiation distance D is set to a desired value. Switching between the single-point irradiation mode and the multi-point irradiation mode is thus made. A vertical position of focal point F at which all laser beams L are condensed has already been known based on specifications (a wavelength of laser beams L and a shape of optical waveguide 44 and lens 45) of laser module 4. Therefore, controller 50 can set irradiation distance D to a desired value by adjusting the height of light source stage 3 from the initial height as appropriate.

In step S7, controller 50 controls power supply 7 to start emission of laser beams L.

In step S8, controller 50 continues irradiation of flat collection kit 10 with laser beams L for a defined time period. The defined time period is, for example, approximately from several ten seconds to several minutes, and it is determined in advance by a user. With this irradiation with light, microscopic objects are collected.

In step S9, controller 50 controls power supply 7 to stop irradiation of flat collection kit 10 with laser beams L. Controller 50 controls illumination apparatus 9 to stop irradiation of flat collection kit 10 with white light WL. A series of processing thus ends.

Figure 12:
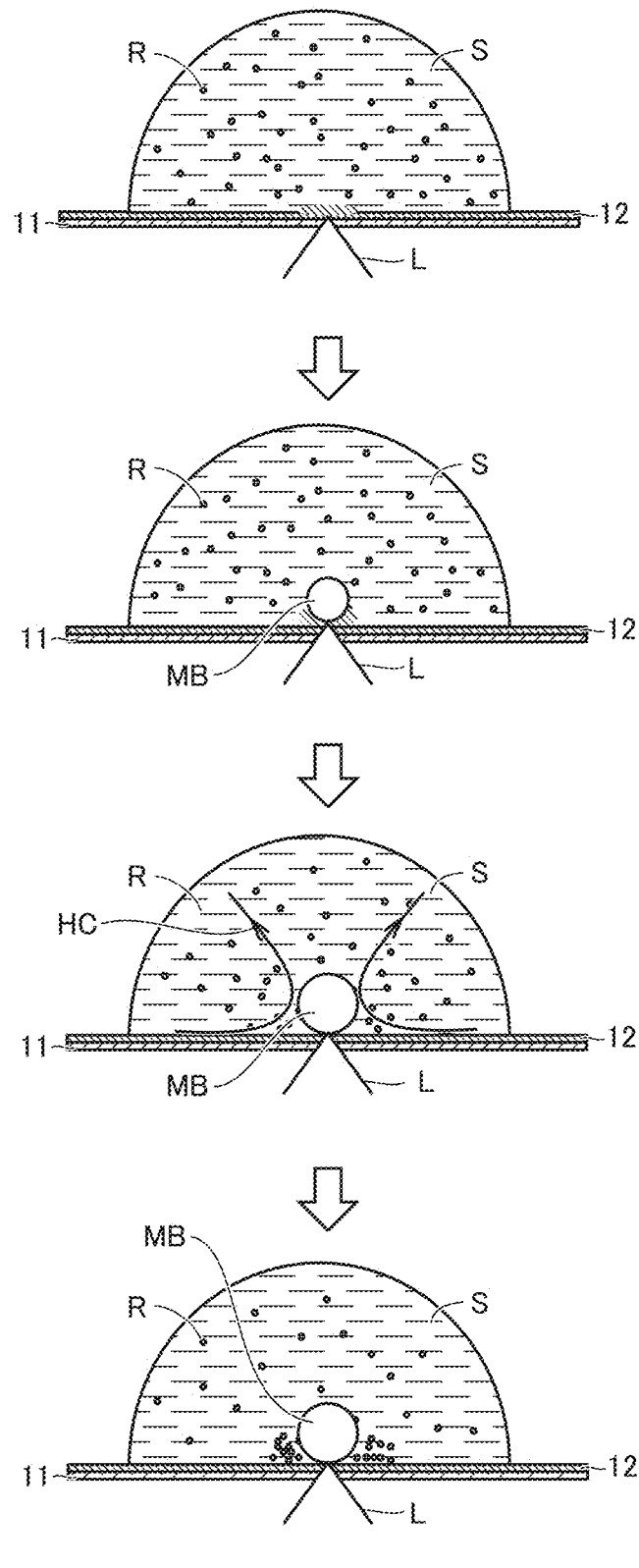
FIG. 12 is a diagram for illustrating a microscopic object collection mechanism in the single-point irradiation mode.
Figure 13:
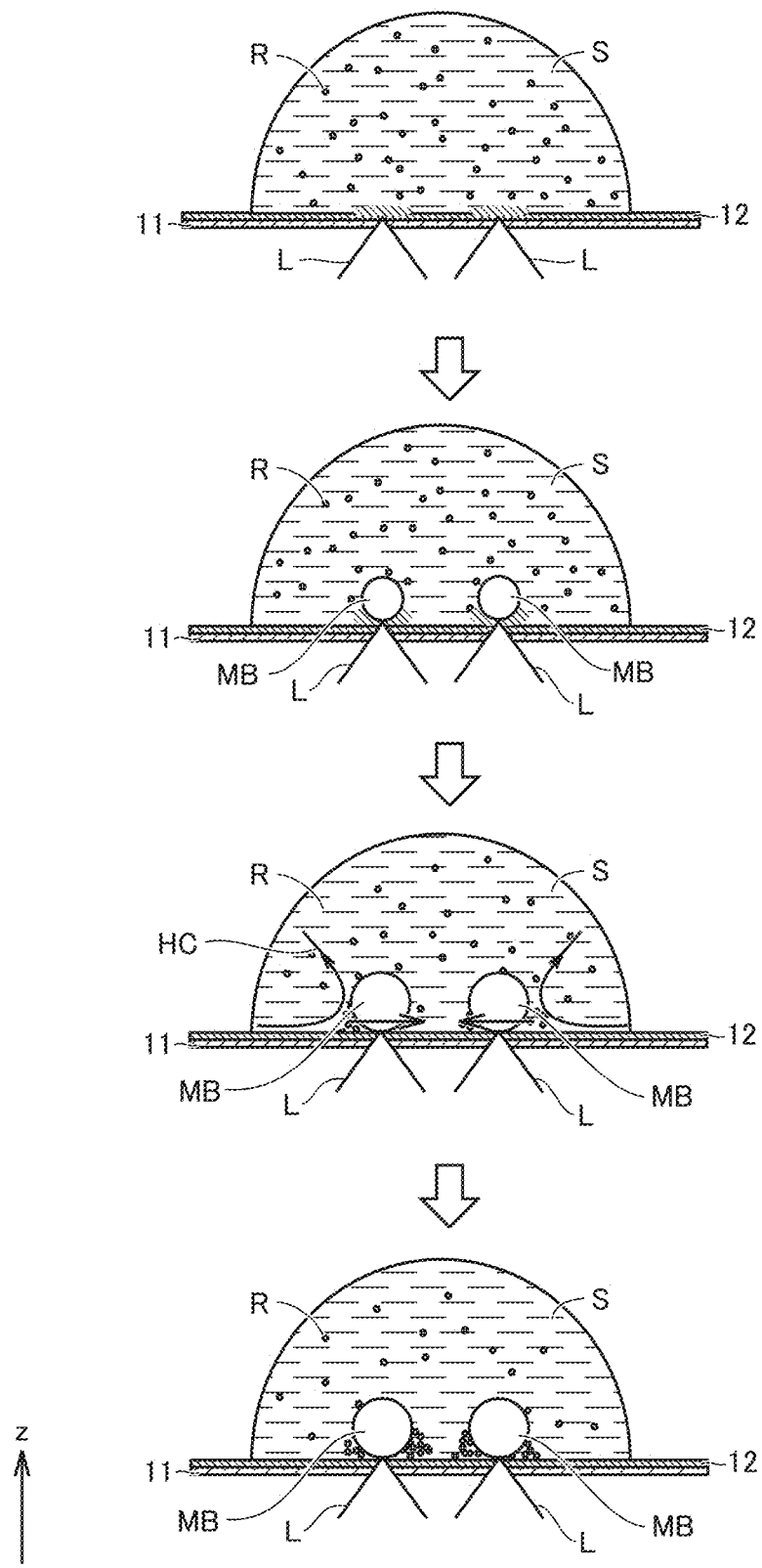
FIG. 13 is a diagram for illustrating the microscopic object collection mechanism in the multi-point irradiation mode.
Figure 17:
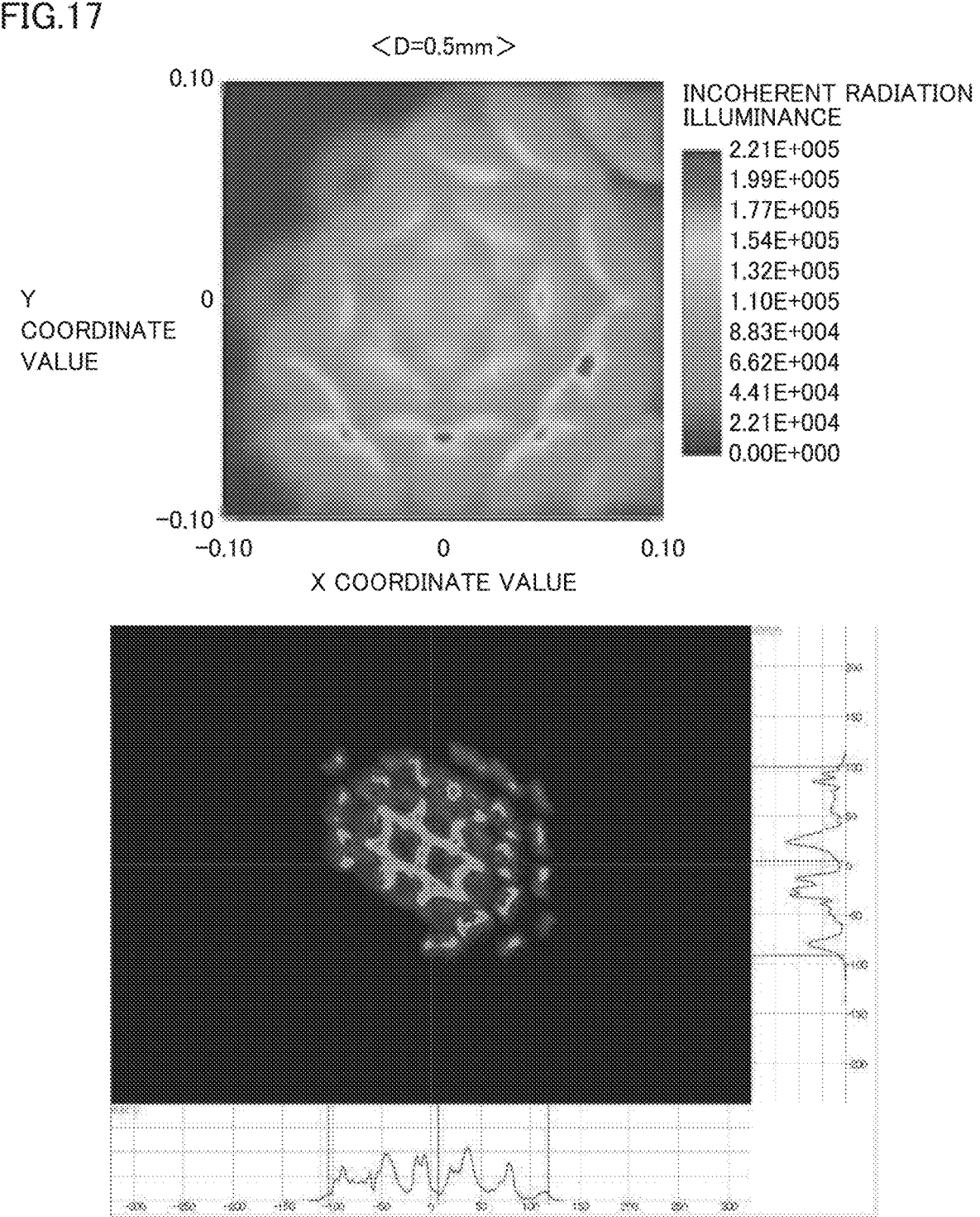
FIG. 17 is a diagram showing a result of optical simulation at an interval between a plurality of laser beams and a result of actual measurement in the vicinity of a laser spot that correspond to an example where irradiation distance D is set to 0.5 mm.
Figure 19:
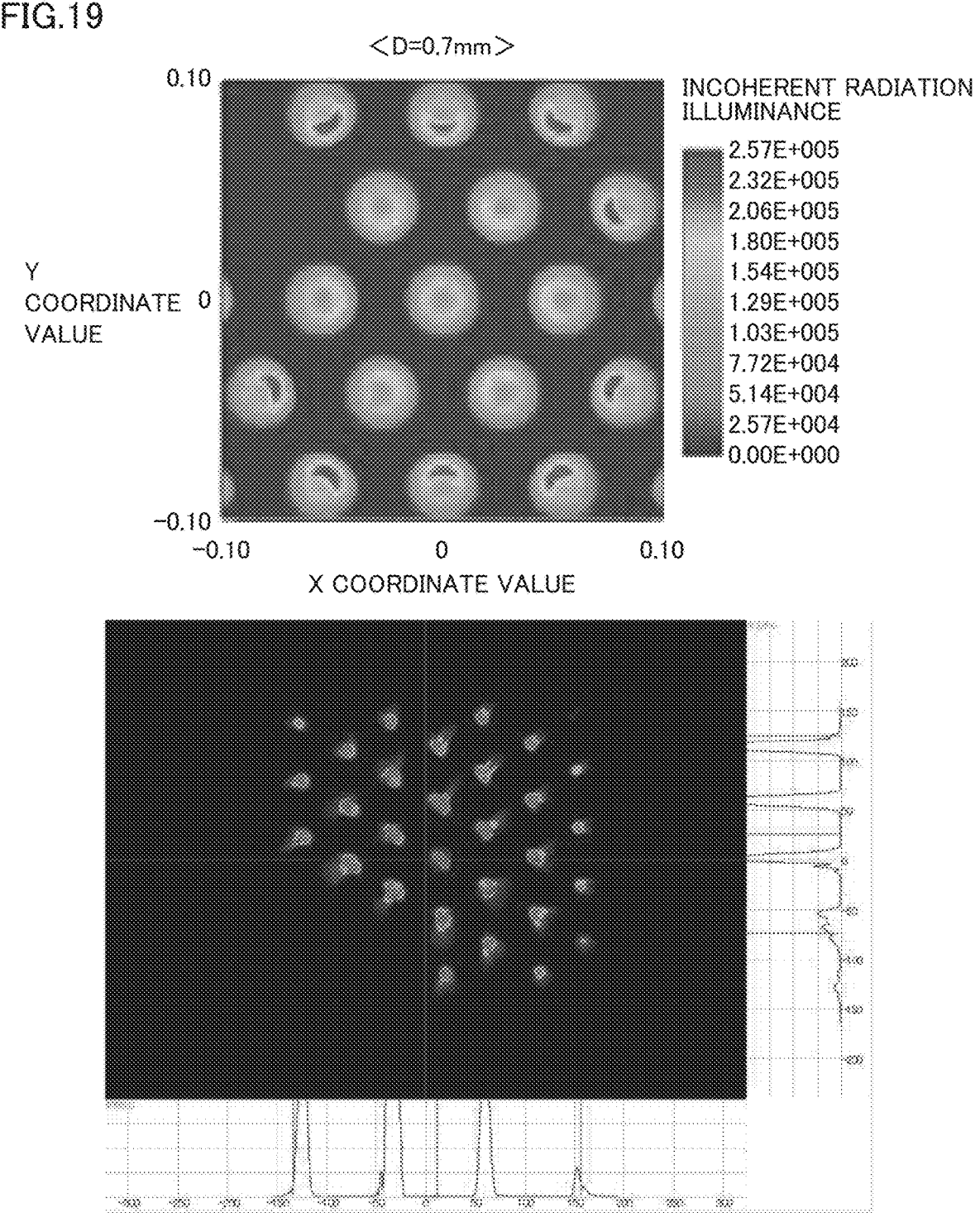
FIG. 19 is a diagram showing a result of optical simulation at an interval between a plurality of laser beams and a result of actual measurement in the vicinity of a laser spot that correspond to an example where irradiation distance D is set to 0.7 mm.
Figure 20:
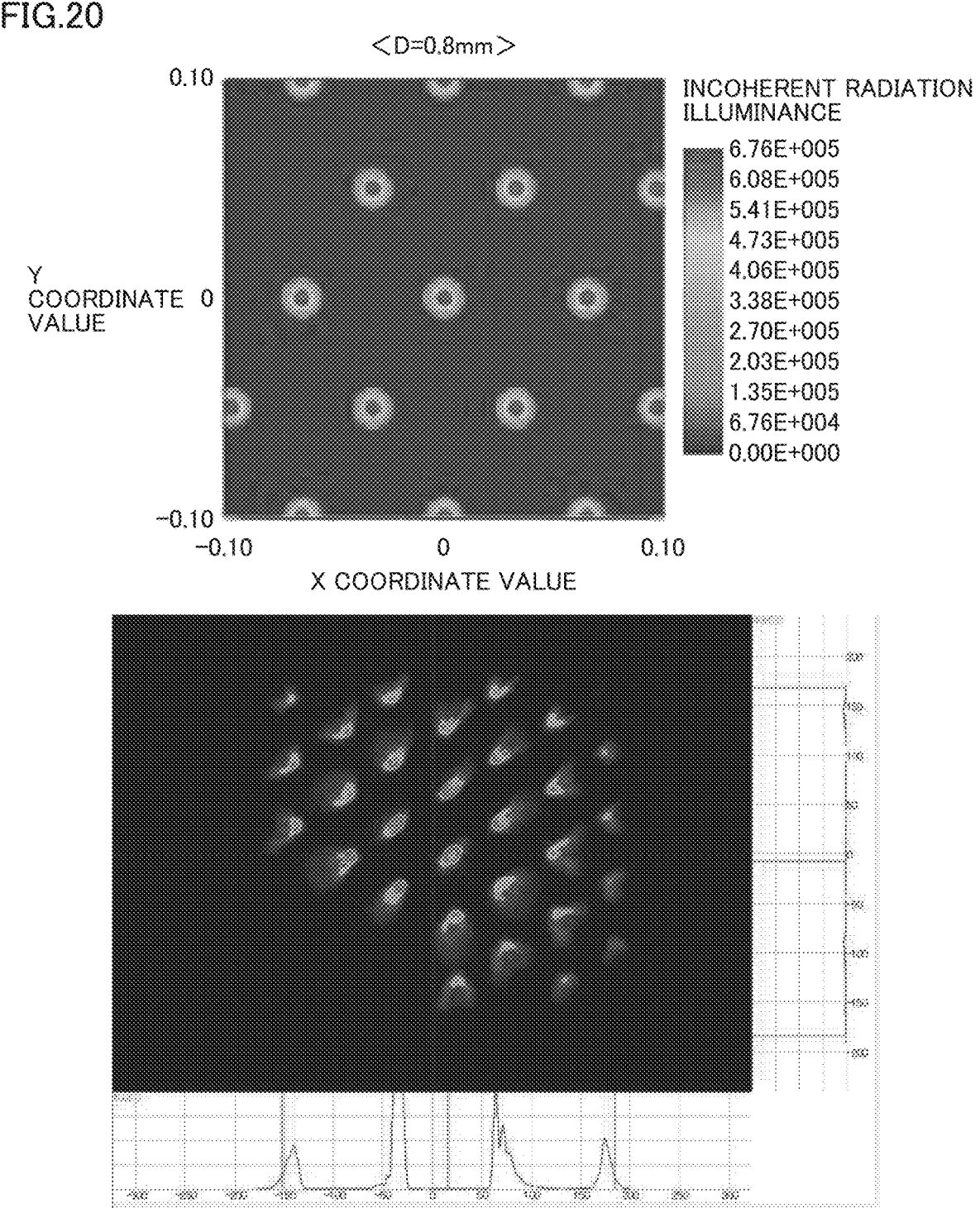
FIG. 20 is a diagram showing a result of optical simulation at an interval between a plurality of laser beams and a result of actual measurement in the vicinity of a laser spot that correspond to an example where irradiation distance D is set to 0.8 mm.
Figure 21:
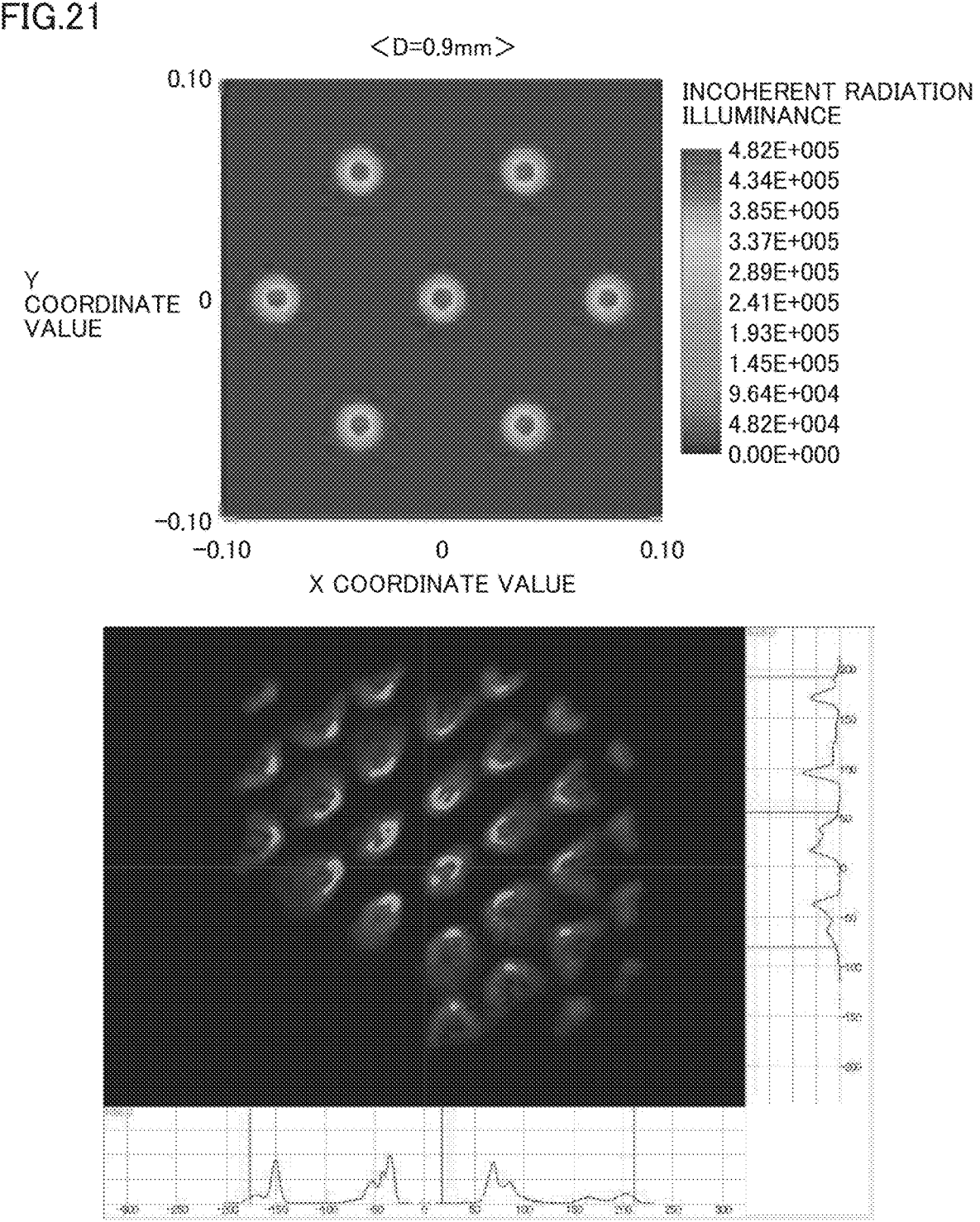
FIG. 21 is a diagram showing a result of optical simulation at an interval between a plurality of laser beams and a result of actual measurement in the vicinity of a laser spot that correspond to an example where irradiation distance D is set to 0.9 mm.
Figure 23:
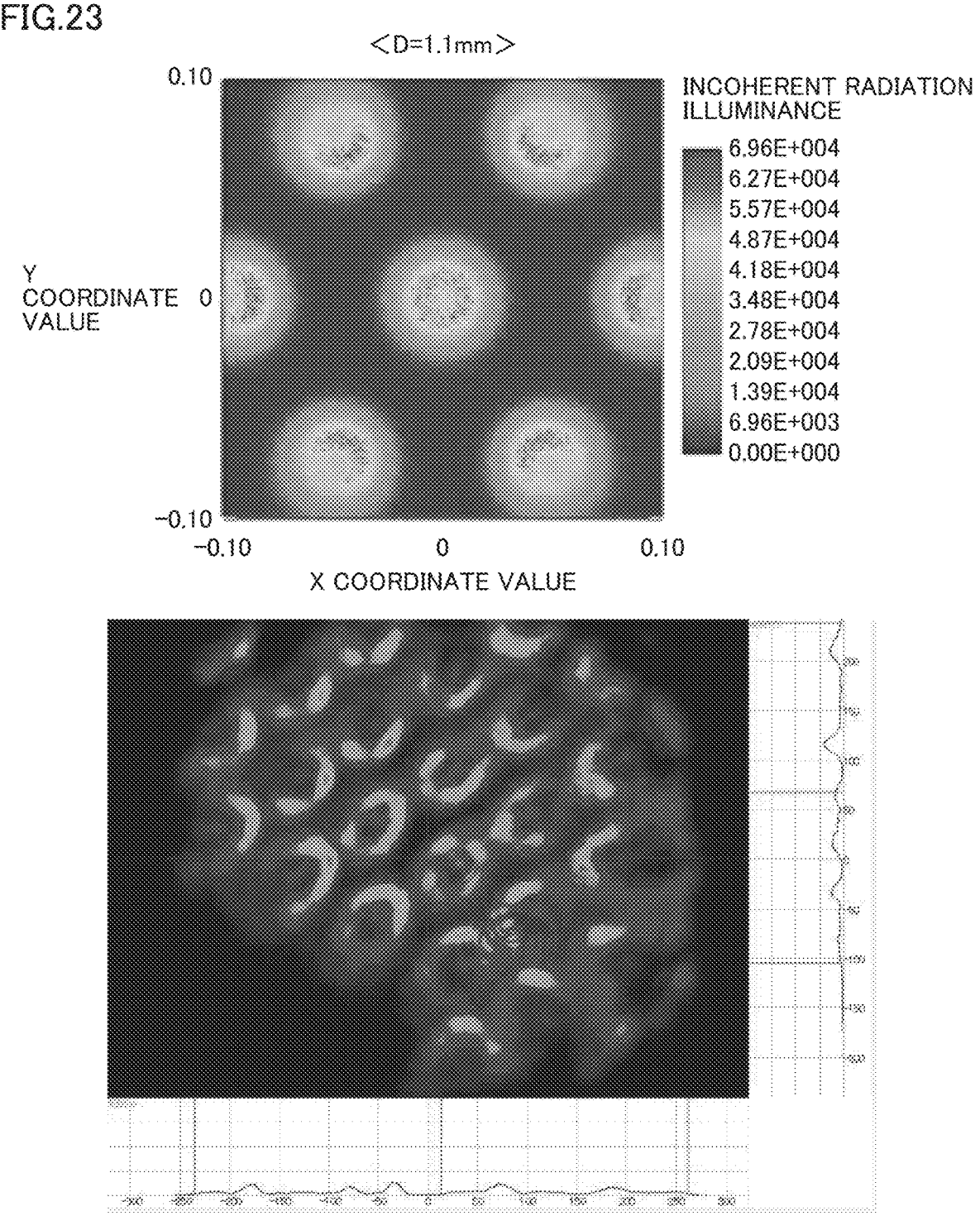
FIG. 23 is a diagram showing a result of optical simulation at an interval between a plurality of laser beams and a result of actual measurement in the vicinity of a laser spot that correspond to an example where irradiation distance D is set to 1.1 mm.

FIG. 12 is a diagram for illustrating a microscopic object collection mechanism in the single-point irradiation mode. FIG. 12 and FIG. 13 which will be described later illustrate contents of processing included in step S8 in further detail.

Referring to FIG. 12, as emission of laser beams L is started, a portion in the vicinity of a laser spot is locally heated owing to the photothermal effect of thin film 12 at the laser spot. Consequently, a dispersion medium of sample S in the vicinity of the laser spot boils and a microbubble MB is produced at the laser spot. Microbubble MB grows over time.

As a position is closer to the laser spot, a temperature of the dispersion medium is higher. In other words, a temperature gradient is produced in the dispersion medium as a result of irradiation with light. Regular heat convection (buoyant convection) is steadily produced in the dispersion medium due to this temperature gradient. A direction of heat convection produced in single-point irradiation is a direction once heading toward microbubble MB and thereafter deviating from microbubble MB as shown with a reference character HC.

Reasons for production of such heat convection can be explained as below. The dispersion medium present above a region where microbubble MB is produced is relatively leaner as a result of heating and moves upward owing to buoyancy. Concurrently, the dispersion medium at a relatively low temperature present horizontally to microbubble MB flows toward microbubble MB.

Microscopic objects are carried over heat convection toward microbubble MB and collected in the vicinity of the laser spot. More specifically, a region where a flow velocity of convection is substantially zero (a stagnation region) is produced between microbubble MB and thin film 12. The microscopic objects carried over heat convection build up in the stagnation region and are collected therein. When irradiation with laser beams L is stopped thereafter, heat convection becomes weaker and soon stops.

FIG. 13 is a diagram for illustrating the microscopic object collection mechanism in the multi-point irradiation mode. In order to avoid complication on the sheet plane, FIG. 13 shows only two laser beams L.

Referring to FIG. 13, in the multi-point irradiation mode, microbubble MB is produced in the vicinity of each of a plurality of laser spots. Depending on the spot interval, adjacent microbubbles MB may merge in a process of growth. Therefore, in the multi-point irradiation mode, microbubbles MB as many as laser spots at the maximum remain. Microscopic objects are carried over heat convection also in the multi-point irradiation mode as in the single-point irradiation mode, and the microscopic objects build up in the stagnation region around each microbubble MB and are collected therein.

According to findings obtained by the present inventors, fast convection is produced toward a gap between adjacent microbubbles MB in the multi-point irradiation mode. Under the influence by this convection, many microscopic objects are collected in the stagnation region produced between adjacent microbubbles MB. Consequently, when a condition for irradiation with light such as laser output is the same between the single-point irradiation mode and the multi-point irradiation mode, the multi-point irradiation mode may be larger in amount of collected microscopic objects.

Result of Optical Simulation and Result of Actual Measurement

In order to confirm switching between single-point irradiation and multi-point irradiation in collection system 100 as described with reference to FIG. 10, various numerical values were allocated to irradiation distance D under a condition that flat collection kit 10 was not provided, and optical simulation of a distribution of illuminance was performed. An image of an actual state of the laser spot at each irradiation distance D was taken with imager 8. In examples shown below, irradiation distance D was varied in increments of 0.1 mm within a range from 0.2 to 1.2 mm.

FIGS. 14 to 24 are diagrams showing results of optical simulation and results of actual measurement in the vicinity of a laser spot when irradiation distance D is set to 0.2 mm to 1.2 mm. In each figure, an upper portion shows a result of optical simulation of the distribution of illuminance and a lower portion shows a result of actual measurement of the distribution of the illuminance.

It can be seen based on comparison between the result of optical simulation and the result of actual measurement in each of FIGS. 14 to 24 that both of them well match with each other. It was confirmed in FIG. 14 that single-point irradiation was realized when the irradiation distance was set to irradiation distance D=0.2 mm. It was confirmed in FIGS. 15 to 24 that multi-point irradiation was realized when the irradiation distance was set to irradiation distance D=0.3 mm to 1.2 mm. It was further confirmed that the spot interval was larger as irradiation distance D was longer.

Figure 25:
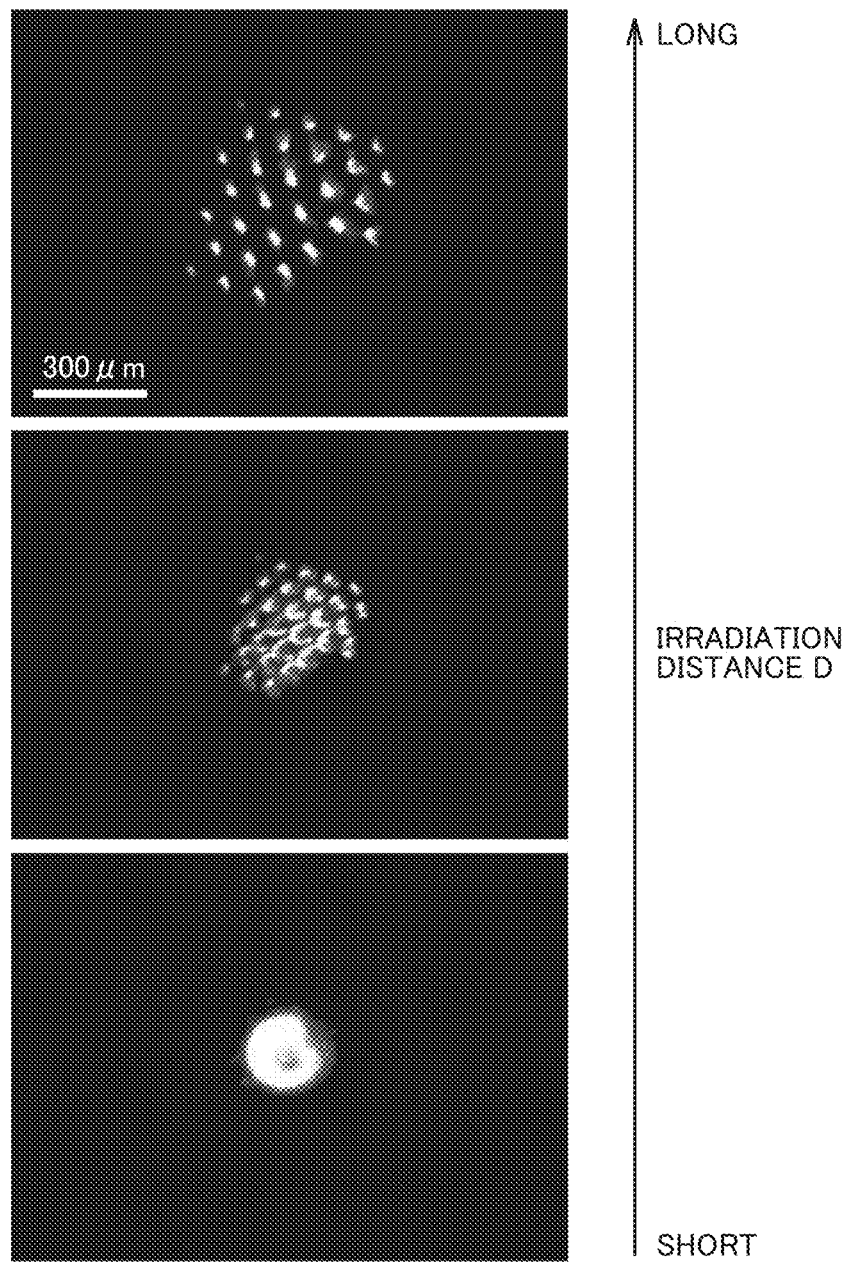
FIG. 25 is a diagram showing a result of observation in the vicinity of the laser spot.

FIG. 25 is a diagram showing a result of observation in the vicinity of the laser spot. As shown in the lowermost image, a spot diameter in a state that irradiation distance D was short and the plurality of laser beams L were completely condensed (the single-point irradiation mode) was approximately 140 μm. This result is in conformity with a theoretical value calculated from the specifications of laser module 4.

Production of Microbubble

A manner of production of microbubble MB in the single-point irradiation mode and the multi-point irradiation mode for honeycomb collection kit 20 was then checked.

Figure 26:
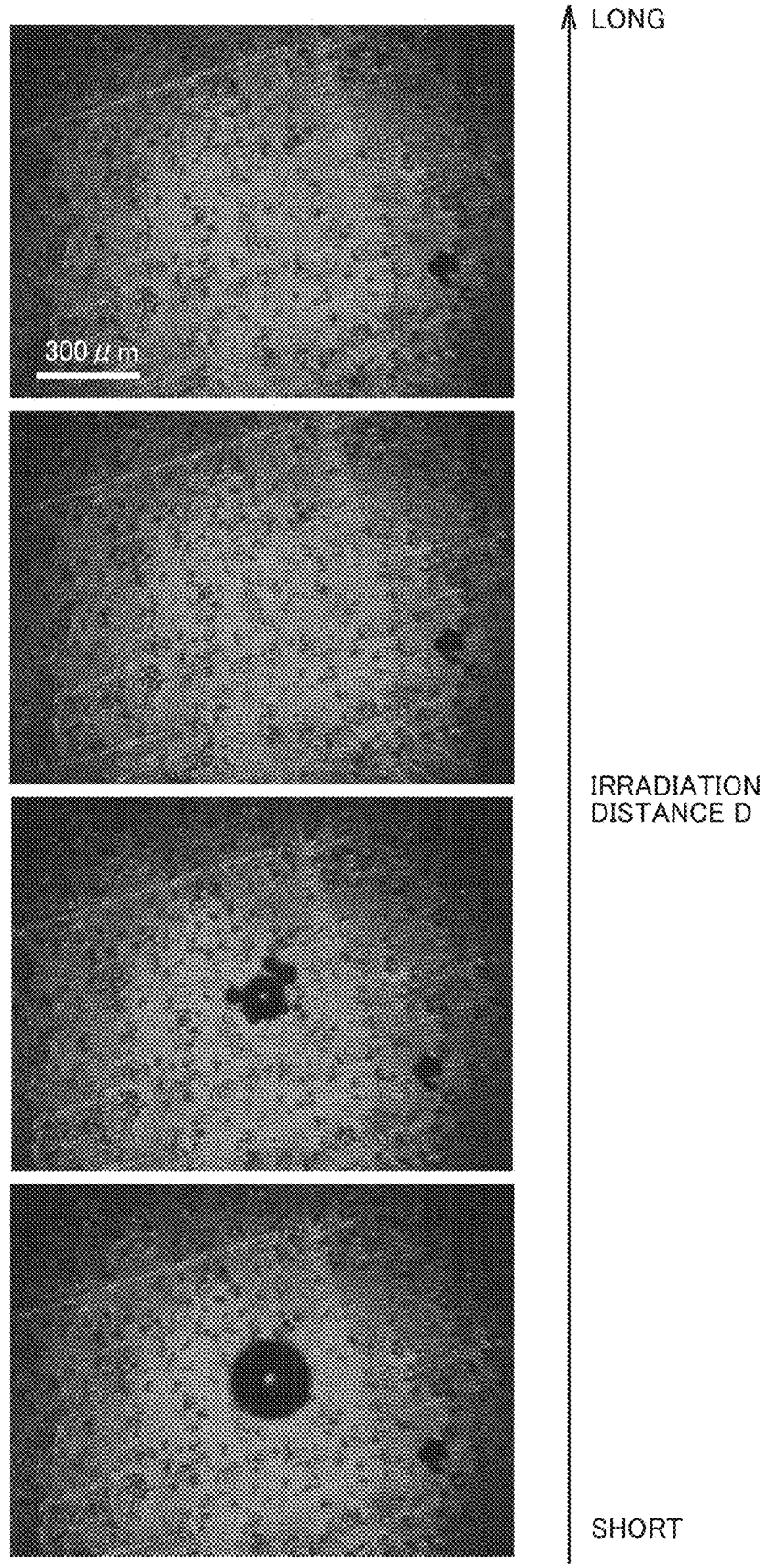
FIG. 26 is a diagram showing a result of observation of a microbubble produced at the time of irradiation of the honeycomb collection kit with light.

FIG. 26 is a diagram showing a result of observation of microbubble MB produced at the time of irradiation of honeycomb collection kit 20 with light. In an example shown in FIG. 26, no microbubble MB was produced when irradiation distance D was long. As irradiation distance D was gradually shorter and the plurality of laser beams L were condensed to some extent, a plurality of small microbubbles MB were produced (the multi-point irradiation mode). As irradiation distance D was further shorter and the plurality of laser beams L were completely condensed, a single large microbubble MB was produced (the single-point irradiation mode).

Result of Collection of Bacteria

In succession, a result of collection of bacteria B in each of the single-point irradiation mode and the multi-point irradiation mode will be described. Output of laser beams that have passed through honeycomb collection kit 20 in the single-point irradiation mode was 180 mW. Total output of laser beams L that have passed through honeycomb collection kit 20 in the multi-point irradiation mode was 180 mW. A time period for irradiation with light was set to twenty seconds in each case. In other words, the condition for irradiation with light was the same between the single-point irradiation mode and the multi-point irradiation mode.

In an example shown below, whether bacteria B collected by irradiation with light were alive or dead was determined based on fluorescent staining of bacteria B. In the present embodiment, SYTO®9 and propidium iodide (PI) were employed as fluorescent dyes. SYTO®9 is a DNA dyeing reagent having membrane permeability, and it dyes DNA regardless of whether or not a cell membrane of bacteria (an outer membrane of *Pseudomonas aeruginosa* representing gram-negative bacteria) has been damaged. In other words, SYTO®9 dyes both of living bacteria (viable bacteria) and dead bacteria (killed bacteria). As bacteria containing SYTO®9 were irradiated with light at an excitation wavelength for SYTO®9, bacteria emit green fluorescence. On the other hand, PI does not have membrane permeability. Therefore, only bacteria (killed bacteria) having the cell membrane damaged were dyed with PI. When PI was externally excited, it emitted red fluorescence. A fluorescence observation image obtained at an excitation wavelength for SYTO®9 is also denoted as a "SYTO®9 image" and a fluorescence observation image obtained at an excitation wavelength for PI is also denoted as a "PI image."

FIG. 27 is a diagram showing a result of observation of honeycomb collection kit 20 in the single-point irradiation mode. FIG. 28 is a diagram showing a result of observation of honeycomb collection kit 20 in the multi-point irradiation mode. FIGS. 27 and 28 each show a perspective image, a SYTO®9 image, and a PI image sequentially from the top.

Referring initially to FIG. 27 showing the result of irradiation with light in the single-point irradiation mode, under the condition for irradiation with light described previously, burning of honeycomb collection kit 20 was observed in the perspective image, which means that the plurality of laser beams L were condensed to one point and temperature increase of honeycomb collection kit 20 was large. In the SYTO®9 image, strong fluorescence was observed at the position of the laser spot. It can thus be seen that many bacteria B were collected around the laser spot and caught in pores 24. Fluorescence in the PI image, however, was also as strong as fluorescence in the SYTO®9 image, which means that many of bacteria caught in pores 24 were killed.

Referring now to FIG. 28 showing the result of irradiation with light in the multi-point irradiation mode, in multi-point irradiation, no burning of honeycomb collection kit 20 was observed in the perspective image. In the SYTO®9 image, strong fluorescence was observed at the plurality of positions of the laser spots as in the single-point irradiation mode.

Fluorescence in the PI image was weaker than in the single-point irradiation mode. It was thus found that a survival rate of bacteria caught in pores 24 was high, reasons for which can be explained as below. In both of the single-point irradiation mode and the multi-point irradiation mode, provided energy is equal. In the multi-point irradiation mode, however, a laser output density (unit of $W/m^2$) at each laser spot is lower than in the single-point irradiation mode. As the distance between the laser spots is longer, heat conduction into pores 24 is suppressed. Therefore, temperature increase within pores 24 in honeycomb collection kit 20 at each laser spot is less. Consequently, in the multi-point irradiation mode, thermal damage to bacteria B can be lessened.

Temperature Distribution in Collection Kit

A result of measurement of a surface temperature of flat collection kit 10 and honeycomb collection kit 20 by thermography will finally be described.

FIG. 29 is a diagram showing a result of measurement of temperature increase by irradiation of flat collection kit 10 with light. FIG. 30 is a diagram showing a result of measurement of temperature increase by irradiation of honeycomb collection kit 20 with light. FIGS. 29 and 30 each show in the upper portion as a comparative example, a result of measurement in irradiation with a single laser beam having a wavelength of 975 nm emitted from a general laser apparatus (not shown). A result of measurement when irradiation distance D of laser module 4 was set to achieve single-point irradiation in the present embodiment is shown in the lower portion. In both of the comparative example and the present embodiment, laser output was set to a common value (180 mW).

Referring to FIG. 29, a highest temperature of flat collection kit 10 was around 70° C. in both of the comparative example and the present embodiment. In the present embodiment, however, an area of a region where the temperature increased was narrower than in the comparative example.

Referring to FIG. 30, in irradiation of honeycomb collection kit 20 with light as well, the highest temperature was around 120° C. in both of the comparative example and the present embodiment as in irradiation of flat collection kit 10 with light, and no great difference was found between the comparative example and the present embodiment. The present embodiment is common in laser output to the comparative example, whereas the spot diameter in the present embodiment is larger than in the comparative example. Therefore, the present embodiment is lower in laser output density at the laser spot than the comparative example. In spite of this fact, in honeycomb collection kit 20, it was observed that the area of the region where the temperature increased in the present embodiment was substantially as large as the area of the region where the temperature increased in the comparative example.

As set forth above, in the present embodiment, laser module 4 including surface emission element 42 representing the VCSEL element, optical waveguide 44 which is the GI type optical fiber, and lens 45 which is the plano convex lens is used. According to the configuration, laser module 4 is designed to condense a plurality of laser beams L to identical focal point F. Therefore, single-point irradiation is realized by adjusting irradiation distance D such that upper surface US (thin film 12) of flat collection kit 10 is located at the same location as focal point F. Multi-point irradiation is realized by adjusting irradiation distance D such that upper surface US of flat collection kit 10 is located at a distance from focal point F.

The single-point irradiation mode and the multi-point irradiation mode are different from each other in manner of production of microbubble MB and heat convection (see FIGS. 12 and 13) and also in laser output density. Therefore, a user can select the single-point irradiation mode when the user desires collection of many microscopic objects around a single microbubble. Alternatively, when the user desires collection of microscopic objects at a plurality of locations over a large area around a large number of microbubbles and/or when the user desires lessened thermal damage to microscopic objects, the user can select the multi-point irradiation mode. Therefore, according to the present embodiment, the user can select a manner of collection of a plurality of microscopic objects dispersed in a liquid.

Furthermore, in laser module 4, surface emission element 42, optical waveguide 44, and lens 45 are integrally formed. By thus packaging (modularizing) laser module 4, collection system 100 can be compact. Utilizing such a characteristic as being compact, a plurality of laser modules 4 may be disposed in an array. By providing a microarray in which a plurality of flat collection kits 10 or a plurality of honeycomb collection kits 20 are disposed in an array above the laser module, collection of microscopic objects in each collection kit can simultaneously proceed. Consequently, microscopic objects can be collected in a shorter period of time.

It should be understood that the embodiments disclosed herein are illustrative and non-restrictive in every respect. The scope of the present disclosure is defined by the terms of the claims rather than the description of the embodiments above and is intended to include any modifications within the scope and meaning equivalent to the terms of the claims.

REFERENCE SIGNS LIST 1 sample stage; 2 sample supply apparatus; 3 light source stage; 4 laser module; 41 substrate; 411 electrode; 42 surface emission element; 421 light source; 43 joint member; 44 optical waveguide; 441 core; 442 clad; 45 lens; 5 cooling apparatus; 6 adjustment mechanism; 7 power supply; 8 imager; 9 illumination apparatus; 50 controller; 10 flat-plate collection kit; 20 honeycomb collection kit; 11, 21 substrate; 12, 23 thin film; 22 honeycomb polymeric film; 24 pore; 25 partition wall; 100 collection system

The invention claimed is:

1. A microscopic object collection system that collects a plurality of microscopic objects dispersed in a liquid, the microscopic object collection system comprising:
    a holder configured to hold a substrate provided with a photothermal conversion region;
    a laser beam source including a plurality of light emission regions, the plurality of light emission regions emitting a plurality of laser beams;
    a condenser lens that condenses the plurality of laser beams to an identical focal point;
    an adjustment mechanism configured to adjust relative positional relation between the holder and the condenser lens; and
    a controller that controls the adjustment mechanism, wherein
    the controller is configured to switch between a single-point irradiation mode and a multi-point irradiation mode, the single-point irradiation mode and the multi-point irradiation mode each being a mode for irradiating the photothermal conversion region with at least one of the plurality of laser beams, the single-point irradiation mode is a mode in which the adjustment mechanism is controlled such that the focal point of the plurality of laser beams falls on the photothermal conversion region, and the multi-point irradiation mode is a mode in which the adjustment mechanism is controlled such that at least some of the plurality of laser beams pass through the photothermal conversion region while the focal point does not fall on the photothermal conversion region.

2. The microscopic object collection system according to claim 1, wherein in the multi-point irradiation mode, the controller sets an interval between the plurality of laser beams emitted to the photothermal conversion region by controlling the adjustment mechanism to adjust a distance between the condenser lens and the photothermal conversion region.

3. The microscopic object collection system according to claim 1, wherein the laser beam source is vertical cavity surface emitting laser.

4. The microscopic object collection system according to claim 1, wherein the condenser lens includes a graded-index optical fiber and a plano convex lens, and the optical fiber includes one end that covers the plurality of light emission regions and the other end joined to a planar side of the plano convex lens.

5. The microscopic object collection system according to claim 1, wherein when the multi-point irradiation mode is selected under a condition that the liquid is prepared on the photothermal conversion region, the controller controls the adjustment mechanism to produce convection over the photothermal conversion region toward (i) a plurality of air bubbles and (ii) a gap between a plurality of air bubbles by emission of the plurality of laser beams, and to collect the plurality of microscopic objects in the gap.

6. A microscopic object collection method of collecting a plurality of microscopic objects dispersed in a liquid, the microscopic object collection method comprising:

preparing the liquid on a photothermal conversion region provided in a substrate;

adjusting relative positional relation between a condenser lens that condenses a plurality of laser beams to an identical focal point and the photothermal conversion region, the adjusting relative positional relation including selectively setting a first state and a second state, the first state being a state in which the relative positional relation is adjusted such that the focal point of the plurality of laser beams falls on the photothermal conversion region, the second state being a state in which the relative positional relation is adjusted such that at least some of the plurality of laser beams pass through the photothermal conversion region while the focal point does not fall on the photothermal conversion region;

producing convection over the photothermal conversion region toward (i) a plurality of air bubbles and (ii) a gap between a plurality of air bubbles by emission of the plurality of laser beams when the second state is selected; and collecting the plurality of microscopic objects in the gap.

7. The microscopic object collection method according to claim 6, wherein in the substrate, a plurality of pores in which the plurality of microscopic objects are caught and a plurality of partition walls each serving as a partition between adjacent pores of the plurality of pores are provided, and the photothermal conversion region is provided to cover at least one of the plurality of pores and the plurality of partition walls.

* * * * *